US006818650B2

(12) United States Patent
Griesgraber

(10) Patent No.: US 6,818,650 B2
(45) Date of Patent: Nov. 16, 2004

(54) 1H-IMIDAZO DIMERS

(75) Inventor: George W. Griesgraber, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/670,957

(22) Filed: Sep. 25, 2003

(65) Prior Publication Data

US 2004/0132766 A1 Jul. 8, 2004

Related U.S. Application Data

(60) Provisional application No. 60/413,848, filed on Sep. 26, 2002.

(51) Int. Cl.$^7$ .................... A61K 31/4745; C07D 471/04
(52) U.S. Cl. ......................... 514/293; 546/82; 546/118; 514/303
(58) Field of Search ............................... 514/293, 303; 546/82, 118

(56) References Cited

U.S. PATENT DOCUMENTS

| | | |
|---|---|---|
| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gerster |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,693,811 A | 12/1997 | Lindstrom |
| 5,741,908 A | 4/1998 | Gerster et al. |
| 5,756,747 A | 5/1998 | Gerster et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,245,776 B1 | 6/2001 | Skwierczynski et al. |
| 6,331,539 B1 | 12/2001 | Crooks et al. |
| 6,376,669 B1 | 4/2002 | Rice et al. |
| 6,451,810 B1 | 9/2002 | Coleman et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,664,265 B2 * | 12/2003 | Crooks et al. ............... 514/293 |
| 2002/0055517 A1 | 5/2002 | Smith |
| 2002/0058674 A1 | 5/2002 | Hedenstrom et al. |

FOREIGN PATENT DOCUMENTS

| | | |
|---|---|---|
| EP | 0 394 026 | 10/1990 |
| EP | 1 104 764 | 6/2001 |
| JP | 9-208584 | 8/1997 |
| JP | 9-255926 | 3/1999 |
| JP | 11-222432 | 8/1999 |
| JP | 2000-247884 | 9/2000 |
| WO | WO 01/74343 | 10/2001 |
| WO | WO 02/36592 | 5/2002 |
| WO | WO 02/46188 | 6/2002 |
| WO | WO 02/46189 | 6/2002 |
| WO | WO 02/46190 | 6/2002 |
| WO | WO 02/46191 | 6/2002 |
| WO | WO 02/46192 | 6/2002 |
| WO | WO 02/46193 | 6/2002 |
| WO | WO 02/46194 | 6/2002 |
| WO | WO 02/46749 | 6/2002 |
| WO | WO 02/102377 | 12/2002 |
| WO | WO 03/020889 | 3/2003 |
| WO | WO 03/043572 | 5/2003 |
| WO | WO 03/045391 | 6/2003 |

OTHER PUBLICATIONS

Wozniak, et al, "The Amination of 3–nitro–1, 5–naphthyridines by Liquid Ammonia/Potassium Permanganate[1,2]. A New and Convenient Amination Method.", *Journal of the Royal Netherlands Chemical Society*, 102, pp 511–513, Dec. 12, 1983.
Brennan, et al, "Automated Bioassay of Interferons in Micro–test Plates", *Biotechniques*, Jun./Jul., 78, 1983.
Testerman, et al., "Cytokine Induction by the Immunomodulators Imiquimod and S–27609", *Journal of Leukocyte Biology*, vol. 58, pp. 365–372, Sep. 1995.
Bachman, et al, "Synthesis of Substituted Quinolylamines. Derivatives of 4–Amino–7–Chloroquinoline", *J. Org. Chem*, 15, pp 1278–1284 (1950).
Jain, et al, "Chemical and Pharmacological Investigations of Some ω–Substituted Alkylamino–3–aminopyridines", *J. Med. Chem*, 11, pp 87–92 (1968).
Baranov, et al., *Chem. Abs.* 85, 94362, (1976).
Berényi, et al, "Ring Transformation of Condensed Dihydro–as–triazines", *J. Heterocyclic Chem.*, 18, pp 1537–1540 (1981).
Chollet, et al, "Development of a Topically Active Imiquimod Formulation", *Pharmaceutical Development and Technology*, 4(1), pp 35–43 (1999).
Izumi, et al., "1*H*–Imidazo[4,5–c]quinoline Derivatives as Novel Potent TNF–α Suppressors: Synthesis and Structure–Activity Relationship of 1–, 2– and 4–Substituted 1*H*–imidazo[4,5–c]pyridines", *Bioorganic & Medicinal Chemistry*, 11, pp 2541–2550 (2003).

* cited by examiner

Primary Examiner—Charanjit S. Aulakh
(74) Attorney, Agent, or Firm—Dean A. Ersfeld

(57) ABSTRACT

1H-imidazo dimer compounds are useful as immune response modifiers. The compounds and compositions of the invention can induce the biosynthesis of various cytokines and are useful in the treatment of a variety of conditions including viral diseases and neoplastic diseases.

23 Claims, No Drawings

1H-IMIDAZO DIMERS

CROSS REFERENCE TO RELATED APPLICATION

This application claims priority to U.S. Provisional Application No. 60/413,848, filed Sep. 26, 2002.

FIELD OF THE INVENTION

The present invention relates to 1H-imidazo dimers and to pharmaceutical compositions containing such dimers. In addition this invention relates to the use of these dimers as immunomodulators, for inducing cytokine biosynthesis in animals, and in the treatment of diseases, including viral and neoplastic diseases. This invention further provides methods of making the dimers and intermediates used in their synthesis.

BACKGROUND OF THE INVENTION

The first reliable report on the 1H-imidazo[4,5-c] quinoline ring system, Bachman et al., *J. Org. Chem.* 15, 1278–1284 (1950) describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c]quinolines were reported. For example, Jain et al., *J. Med. Chem.* 11, pp. 87–92 (1968), synthesized the compound 1-[2-(4-piperidyl) ethyl]-1H-imidazo[4,5-c]quinoline as a possible anticonvulsant and cardiovascular agent. Also, Baranov et al., *Chem. Abs.* 85, 94362 (1976), have reported several 2-oxoimidazo [4,5-c]quinolines, and Berenyi et al., *J. Heterocyclic Chem.* 18, 1537–1540 (1981), have reported certain 2-oxoimidazo [4,5-c]quinolines.

Certain 1H-imidazo[4,5-c]quinolin-4-amines and 1- and 2-substituted derivatives thereof were later found to be useful as antiviral agents, bronchodilators and immunomodulators. These are described in, inter alia, U.S. Pat. Nos. 4,689,338; 4,698,348; 4,929,624; 5,037,986; 5,268,376; 5,346,905; and 5,389,640, all of which are incorporated herein by reference.

Many imidazoquinoline amine, imidazopyridine amine, 6,7-fused cycloalkylimidazopyridine amine, 1,2-bridged imidazoquinoline amine, thiazoloquinoline amine, oxazoloquinoline amine, thiazolopyridine amine, oxazolopyridine amine, imidazonaphthyridine and tetrahydroimidazonaphthyridine amine compounds have demonstrated potent immunostimulating, antiviral and antitumor (including anticancer) activity, and have also been shown to be useful as vaccine adjuvants to enhance protective immune system response to vaccines. Such compounds and methods of making them are disclosed in, for example, U.S. Pat. Nos. 4,689,338; 4,929,624; 5,266,575; 5,268,376; 5,352,784; 5,389,640; 5,482,936; 5,494,916; 6,110,929; 6,194,425; 6,331,539; 6,376,669; 6,451,810; 6,541,485; 6,573,273; 6,545,016; 6,545,017; and 6,525,064, and PCT Publications WO 02/46188, WO 02/46189; WO 02/46190; WO 02/46191; WO 02/46192; and WO 02/46193, the disclosures of which are specifically incorporated by reference herein.

Despite these recent discoveries of compounds that are useful as immune response modifiers, there is a continuing need for compounds that have the ability to modulate the immune response, by induction of cytokine biosynthesis or other mechanisms.

SUMMARY OF THE INVENTION

It has now been found that certain 1H-imidazo dimer compounds induce cytokine biosynthesis. In one aspect, the present invention provides 1H-imidazo dimer compounds of the Formula (I):

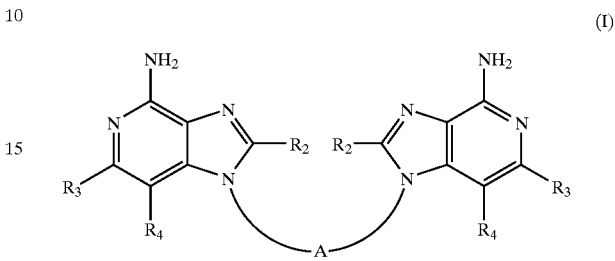

wherein A, $R_2$, $R_3$ and $R_4$ are as defined herein.

The compounds of Formula I are useful as immune response modifiers (IRMs) due to their ability to induce cytokine biosynthesis (e.g., induce the biosynthesis or production of one or more cytokines) and otherwise modulate the immune response when administered to animals. This makes the compounds useful in the treatment of a variety of conditions such as viral diseases, and neoplastic diseases, that are responsive to such changes in the immune response.

In another aspect, the present invention provides pharmaceutical compositions containing the immune response modifier compounds, and methods of inducing cytokine biosynthesis in an animal, treating a viral disease in an animal, and treating a neoplastic disease in an animal, by administering an effective amount of one or more compounds of Formula I and/or pharmaceutically acceptable salts thereof to the animal.

In addition, the invention provides methods of synthesizing the compounds of the invention and intermediates useful in the synthesis of these compounds.

As used herein, "a," "an," "the," "at least one," and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF THE INVENTION

In one aspect, the present invention provides 1H-imidazo dimer compounds of the Formula (I):

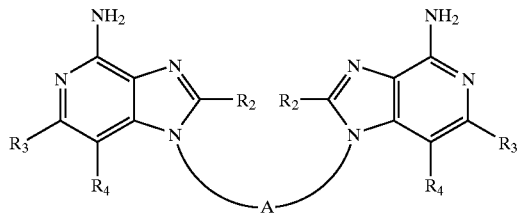

wherein:
A is a divalent linking group selected from the group consisting of:
straight or branched chain $C_{4-20}$ alkylene;
straight or branched chain $C_{4-20}$ alkenylene;
straight or branched chain $C_{4-20}$ alkynylene; and
—Z—Y—W—Y—Z—;
each Z is independently selected from the group consisting of
straight or branched chain $C_{2-20}$ alkylene;
straight or branched chain $C_{4-20}$ alkenylene; and
straight or branched chain $C_{4-20}$ alkynylene;
any of which may be optionally interrupted by —O—, —N($R_5$)—, or —S(O)$_2$—;
each Y is independently selected from the group consisting of:
a bond;
—N($R_5$)C(O)—;
—C(O)N($R_5$)—;
—N($R_5$)C(O)N($R_5$)—;
—N($R_5$)S(O)$_2$—;
—S(O)$_2$N($R_5$)—;
—OC(O)O—;
—OC(O)—;
—C(O)O—;
—N($R_5$)C(O)O—; and
—OC(O)N($R_5$)—;
W is selected from the group consisting of:
straight or branched chain $C_{2-20}$ alkylene;
straight or branched chain $C_{2-20}$ alkenylene;
straight or branched chain $C_{4-20}$ alkynylene;
straight or branched chain perfluoro $C_{2-20}$ alkylene;
$C_{1-4}$ alkylene-O—$C_{1-4}$ alkylene;
—C(O)—;
—S(O)$_2$—;
—OC(O)O—;
—N($R_5$)C(O)N($R_5$)—;

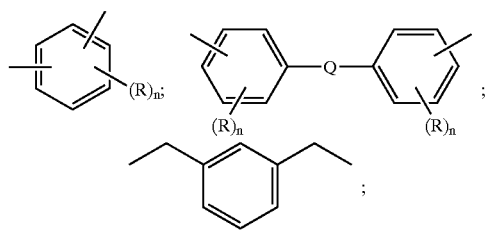

1,5-naphthylene;
2,6-pyridinylene;
1,2-cyclohexylene;
1,3-cyclohexylene;
1,4-cyclohexylene;
trans-1,4-cyclohexylene;

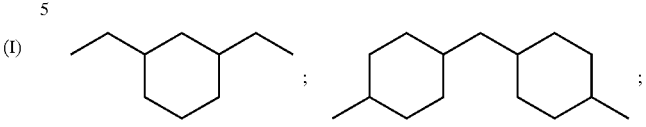

and
trans-5-norbornen-2,3-diyl;
wherein n is 0–4; each R is independently selected from the group consisting of $C_{1-4}$ alkyl, $C_{1-4}$ alkoxy, and halogen; and Q is selected from the group consisting of a bond, —CH$_2$—, and —O—;
$R_2$ is selected from the group consisting of:
-hydrogen;
-alkyl;
-alkenyl;
-aryl;
-substituted aryl;
-heteroaryl;
-substituted heteroaryl;
-alkyl-X-alkyl;
-alkyl-X-aryl;
-alkyl-X-alkenyl; and
-alkyl or alkenyl substituted by one or more substituents selected from the group consisting of:
—OH;
-halogen;
—N($R_6$)$_2$;
—C(O)—N($R_6$)$_2$;
—C(S)—N($R_6$)$_2$;
—S(O)$_2$—N($R_6$)$_2$;
—N($R_6$)—C(O)—$C_{1-10}$ alkyl;
—N($R_6$)—C(S)—$C_{1-10}$ alkyl;
—N($R_6$)—S(O)$_2$—$C_{1-10}$ alkyl;
—C(O)—$C_{1-10}$ alkyl;
—C(O)—O—$C_{1-10}$ alkyl;
—N$_3$;
-aryl;
-substituted aryl;
-heteroaryl;
-substituted heteroaryl;
-heterocyclyl;
-substituted heterocyclyl;
—C(O)-aryl;
—C(O)-(substituted aryl);
—C(O)-heteroaryl; and
—C(O)-(substituted heteroaryl);
$R_3$ and $R_4$ are each independently selected from the group consisting of:
-hydrogen;
-halogen;
-alkyl;
-alkenyl;
-X-alkyl; and
—N($R_6$)$_2$;
or when taken together, $R_3$ and $R_4$ form a fused aryl or heteroaryl ring that is unsubstituted or substituted by one or more substituents selected from the group consisting of:
-halogen;
-alkyl;
-alkenyl;

-X-alkyl; and
—N(R$_6$)$_2$;
or when taken together, R$_3$ and R$_4$ form a fused 5 to 7 membered saturated ring, containing 0 to 2 heteroatoms and unsubstituted or substituted by one or more substituents selected from the group consisting of:
-halogen;
-alkyl;
-alkenyl;
-X-alkyl; and
—N(R$_6$)$_2$;
each R$_5$ is independently selected from the group consisting of:
hydrogen;
C$_{1-6}$ alkyl;
C$_{3-7}$ cycloalkyl; and
benzyl; or
when Y is —N(R$_5$)C(O)—, —C(O)N(R$_5$)—, —N(R$_5$)C(O)N(R$_5$)—, —N(R$_5$)S(O)$_2$—, —S(O$_2$)N(R$_5$)—, —N(R$_5$)C(O)O—, or —OC(O)N(R$_5$)— and the nitrogen of the N(R$_5$) group is bonded to Z, then R$_5$ can join with Z to form a ring having the structure

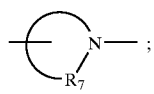

each R$_6$ is independently hydrogen or C$_{1-10}$ alkyl;
R$_7$ is C$_{3-8}$ alkylene; and
X is —O— or —S—;
with the proviso that if W is —C(O)—, —S(O)$_2$—, —OC(O)O—, or —N(R$_5$)C(O)N(R$_5$)— then each Y is a bond;
or a pharmaceutically acceptable salt thereof.

The present invention also provides compounds that are useful as intermediates in the synthesis of compounds of Formula (I). These intermediate compounds have the structural Formulas (II)–(V), described below.

The present invention provides intermediate compounds of the Formula (II):

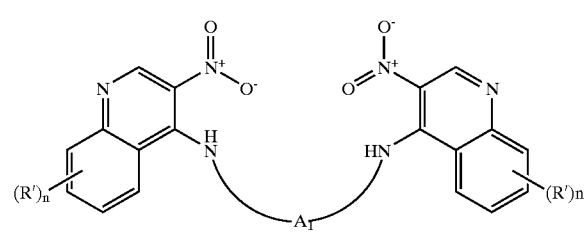

(II)

wherein:
A$_1$ is a divalent linking group selected from the group consisting of:
straight or branched chain C$_{4-20}$ alkylene;
straight or branched chain C$_{4-20}$ alkenylene; and
straight or branched chain C$_{4-20}$ alkynylene;
any of which may be optionally interrupted by —S(O)$_2$— or a protected
—C(O)—;
n is 0 to 4;
each R' present is independently selected from the group consisting of:
halogen;
alkyl;
alkenyl; and
—O-alkyl;
or a pharmaceutically acceptable salt thereof The present invention also provides intermediate compounds of the Formula (III):

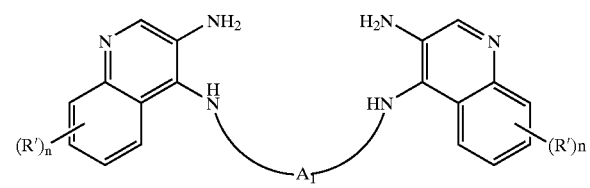

(III)

wherein:
A$_1$ is a divalent linking group selected from the group consisting of:
straight or branched chain C$_{4-20}$ alkylene;
straight or branched chain C$_{4-20}$ alkenylene; and
straight or branched chain C$_{4-20}$ alkynylene;
any of which may be optionally interrupted by —S(O)$_2$— or a protected
—C(O)—;
n is 0 to 4;
each R' present is independently selected from the group consisting of:
halogen;
alkyl;
alkenyl; and
—O-alkyl;
or a pharmaceutically acceptable salt thereof.

The present invention also provides intermediate compounds of Formula (IV):

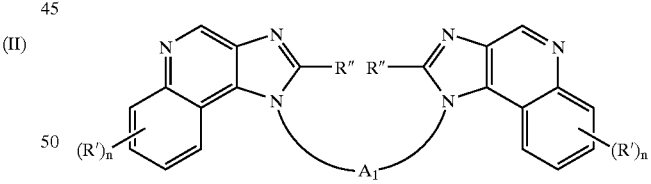

(IV)

wherein:
A$_1$ is a divalent linking group selected from the group consisting of:
straight or branched chain C$_{4-20}$ alkylene;
straight or branched chain C$_{4-20}$ alkenylene; and
straight or branched chain C$_{4-20}$ alkynylene;
any of which may be optionally interrupted by —S(O)$_2$— or a protected —C(O)—;
R" is selected from the group consisting of:
-hydrogen;
-alkyl;
-alkenyl;
-aryl;
-substituted aryl;

-heteroaryl;
-substituted heteroaryl;
-alkyl-O-alkyl;
-alkyl-O-aryl;
-alkyl-O-alkenyl; and
-alkyl or alkenyl substituted by one or more substituents selected from the group consisting of:
—OH;
-halogen;
—C(O)—N($R_6$)$_2$;
—C(S)—N($R_6$)$_2$;
—S(O)$_2$—N($R_6$)$_2$;
—N($R_6$)—C(O)—$C_{1-10}$ alkyl;
—N($R_6$)—C(S)—$C_{1-10}$ alkyl;
—N($R_6$)—S(O)$_2$—$C_{1-10}$ alkyl;
—C(O)—$C_{1-10}$ alkyl;
—C(O)—O—$C_{1-10}$ alkyl;
—N$_3$;
-aryl;
-substituted aryl,
-heteroaryl;
-substituted heteroaryl;
-heterocyclyl;
-substituted heterocyclyl;
—C(O)-aryl;
—C(O)-(substituted aryl);
—C(O)-heteroaryl; and
—C(O)-(substituted heteroaryl);

n is 0 to 4;

each R' present is independently selected from the group consisting of:
halogen;
alkyl;
alkenyl; and
—O-alkyl;

each $R_6$ is independently hydrogen or $C_{1-10}$ alkyl; or a pharmaceutically acceptable salt thereof The present invention also provides intermediate compounds of the Formula (V):

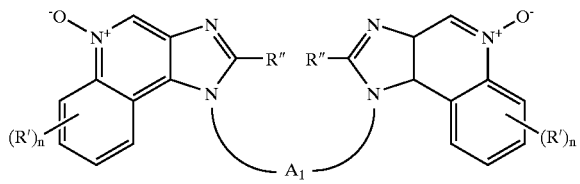

(V)

wherein:
$A_1$ is a divalent linking group selected from the group consisting of:
straight or branched chain $C_{4-20}$ alkylene;
straight or branched chain $C_{4-20}$ alkenylene; and
straight or branched chain $C_{4-20}$ alkynylene;
any of which may be optionally interrupted by —S(O)$_2$— or a protected —C(O)—;
R" is selected from the group consisting of:
-hydrogen;
-alkyl;
-alkenyl;
-aryl;
-substituted aryl;
-heteroaryl;
-substituted heteroaryl;
-alkyl-O-alkyl;
-alkyl-O-aryl;
-alkyl-O-alkenyl; and
-alkyl or alkenyl substituted by one or more substituents selected from the group consisting of:
—OH;
-halogen;
—C(O)—N($R_6$)$_2$;
—C(S)—N($R_6$)$_2$;
—S(O)$_2$—N($R_6$)$_2$;
—N($R_6$)—C(O)—$C_{1-10}$ alkyl;
—N($R_6$)—C(S)—$C_{1-10}$ alkyl;
—N($R_6$)—S(O)$_2$—$C_{1-10}$ alkyl;
—C(O)—$C_{1-10}$ alkyl;
—C(O)—O—$C_{1-10}$ alkyl;
—N$_3$;
-aryl;
-substituted aryl;
-heteroaryl;
-substituted heteroaryl;
-heterocyclyl;
-substituted heterocyclyl;
—C(O)-aryl;
—C(O)-(substituted aryl);
—C(O)-heteroaryl; and
—C(O)-(substituted heteroaryl);

n is 0 to 4;

each R' present is independently selected from the group consisting of:
halogen;
alkyl;
alkenyl; and
—O-alkyl;

each $R_6$ is independently hydrogen or $C_{1-10}$ alkyl;
or a pharmaceutically acceptable salt thereof In some embodiments of the present invention A is straight or branched chain $C_{4-20}$ alkylene.

In other embodiments of the present invention A is —Z—Y—W—Y—Z—. In certain embodiments each Z is straight or branched chain $C_{2-20}$ alkylene optionally interrupted by —O—. In certain embodiments each Z is selected from the group consisting of straight or branched chain $C_{2-4}$ alkylene and $C_{1-4}$ alkylene-O—$C_{1-4}$ alkylene. In certain embodiments $R_5$ is joined with Z to form a ring having the structure

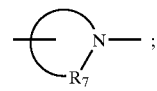

wherein $R_7$ is $C_{4-6}$ alkylene.

In certain embodiments each Y is independently selected from the group consisting of a bond; —N($R_5$)C(O)—; —C(O)N($R_5$)—; —N($R_5$)C(O)N($R_5$)—; —S(O)$_2$N($R_5$)—; and —N($R_5$)S(O)$_2$—.

In certain embodiments W is selected from the group consisting of straight or branched chain $C_{2-20}$ alkylene; —N($R_5$)C(O)N($R_5$)—;

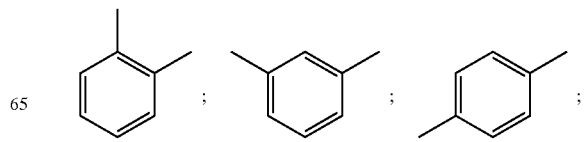

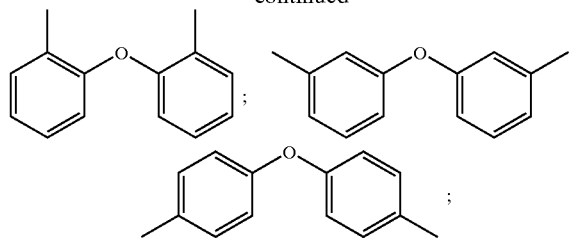

2-cyclohexylene; 1,3-cyclohexylene; 1,4-cyclohexylene; and trans-1,4-cyclohexylene.

In some embodiments of the present invention $R_5$ is hydrogen.

In some embodiments of the present invention $R_2$ is hydrogen, alkyl or alkyl-O-alkyl. In certain embodiments $R_2$ is hydrogen, methyl, ethyl, propyl, butyl, cyclopropylmethyl, ethoxymethyl or methoxyethyl.

In some embodiments of the present invention $R_3$ and $R_4$ join together to form a fused benzene ring. In other embodiments $R_3$ and $R_4$ join together to form a fused pyridine ring. In other embodiments $R_3$ and $R_4$ join together to form a fused six membered saturated ring. In other embodiments $R_3$ and $R_4$ join together to form a fused six membered saturated ring containing one nitrogen atom. In still other embodiments of the present invention $R_3$ and $R_4$ are independently hydrogen or alkyl.

The invention is inclusive of the compounds described herein in any of their pharmaceutically acceptable forms, including isomers such as diastereomers and enantiomers, salts, solvates, polymorphs, and the like. In particular, if a compound is optically active, the invention specifically includes each of the compound's enantiomers as well as racemic mixtures of the enantiomers.

Preparation of the Compounds

Compounds of the invention can be prepared according to Reaction Scheme I wherein R', R", $A_1$ and n are as defined above.

In step (1) of Reaction Scheme I a 4-chloro-3-nitroquinoline of Formula VI is reacted with a diamine of Formula VII to provide a dimer compound of Formula II. The reaction can be carried out by adding a diamine of Formula VII to a solution of a compound of Formula VI in a suitable solvent such as dichloromethane in the presence of a base such as triethylamine. The reaction can be run at ambient temperature. Many compounds of Formula VI are known or can be prepared using known synthetic methods, see for example, U.S. Pat. Nos. 4,689,338; 5,175,296; 5,367,076; 5,389,640; and 6,194,425 and the references cited therein. Many diamines of Formula VII are commercially available; others can be readily prepared using known synthetic methods.

In step (2) of Reaction Scheme I a compound of Formula II is reduced to provide a compound of Formula III. The reduction can be carried out using a conventional heterogeneous hydrogenation catalyst. The reaction can be conveniently carried out on a Parr apparatus in a suitable solvent such as toluene. In those instances where $A_1$ contains an alkenylene or alkynylene group a catalyst is selected that is capable of reducing the nitro group without reducing the alkenylene or alkynylene group, examples include tin and zinc/hydrochloric acid.

In step (3) of Reaction Scheme I a compound of Formula III is (i) reacted with an acyl chloride of Formula $R_2C(O)Cl$ and then (ii) cyclized to provide a 1H-imidazo dimer compound of Formula IV. In part (i) the acyl chloride is added to a solution of a compound of Formula III in a suitable solvent such as dichloromethane in the presence of a base such as triethylamine. The reaction can be run at ambient temperature. In part (ii) the product of part (i) is heated in an alcoholic solvent in the presence of a base. Preferably the product of part (i) is refluxed in ethanol in the presence of excess triethylamine or is heated with methanolic ammonia.

Alternatively, step (3) can be carried out by reacting a compound of Formula III with a carboxylic acid or an equivalent thereof. Suitable equivalents to carboxylic acid include orthoesters and 1,1-dialkoxyalkyl alkanoates. The carboxylic acid or equivalent is selected such that it will provide the desired $R_2$ substituent in a compound of Formula IV. For example, triethyl orthoformate will provide a compound where $R_2$ is hydrogen and triethyl orthovalerate will provide a compound where $R_2$ is butyl. The reaction can be run in the absence of solvent or in an inert solvent such as toluene. The reaction is run with sufficient heating to drive off any alcohol or water formed as a byproduct of the reaction. Optionally a catalyst such as pyridine hydrochloride can be included.

In step (4) of Reaction Scheme I a 1H-imidazo dimer compound of Formula IV is oxidized to provide an N-oxide of Formula V using a conventional oxidizing agent that is capable of forming N-oxides. Preferably a solution of a compound of Formula IV in a suitable solvent such as dichloromethane is treated with 3-chloroperoxybenzoic acid at ambient temperature.

In step (5) of Reaction Scheme I an N-oxide of Formula V is aminated to provide a 1H-imidazo dimer compound of Formula VIII, which is a subgenus of Formula I. The reaction is carried out in two parts. In part (i) a compound of Formula V is reacted with an acylating agent. Suitable acylating agents include alkyl- or arylsulfonyl chorides (e.g., benzenesulfonyl choride, methanesulfonyl choride, and p-toluenesulfonyl chloride). In part (ii) the product of part (i) is reacted with an excess of an aminating agent. Suitable animating agents include ammonia (e.g. in the form of ammonium hydroxide) and ammonium salts (e.g., ammonium carbonate, ammonium bicarbonate, ammonium phosphate). The reaction can be carried out by dissolving a compound of Formula V in a suitable solvent such as dichloromethane, adding ammonium hydroxide to the solution, and then adding p-toluenesulfonyl chloride. The product or a pharmaceutically acceptable salt thereof can be isolated using conventional methods. When At contains a —C(O)— group, the group is protected (e.g, by forming an acetal) throughout the synthesis and then the protecting group is removed.

Reaction Scheme I

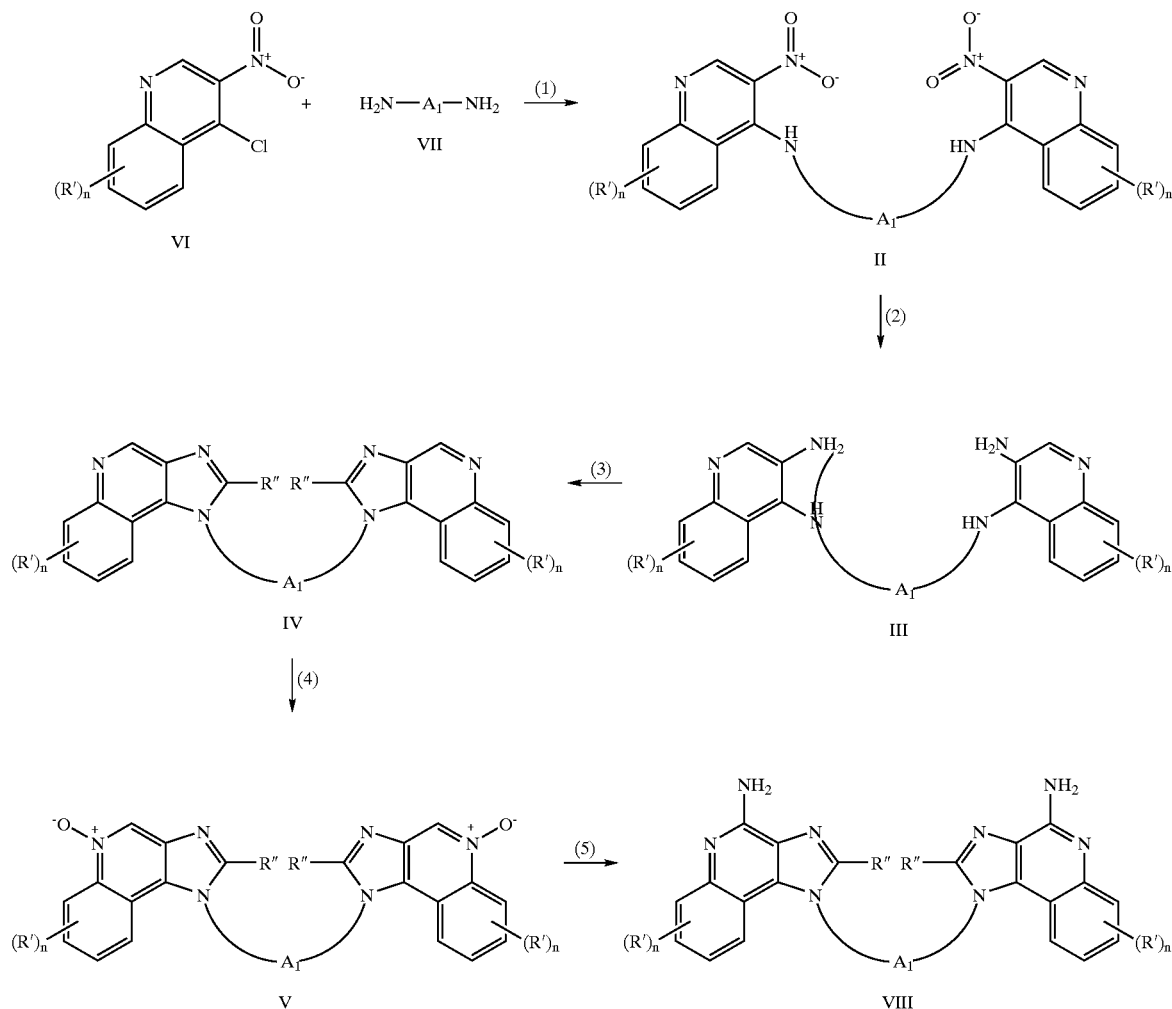

Compounds of the invention can also be prepared according to Reaction Scheme II wherein $R_2$, $R_3$, $R_4$, $R_5$ and Z are as defined above and $W_1$ is selected from the group consisting of straight or branched chain $C_{2-20}$ alkylene; straight or branched chain $C_{4-20}$ alkenylene; straight or branched chain $C_{4-20}$ alkynylene; straight or branched chain perfluoro $C_{2-20}$ alkylene; $C_{1-4}$ alkylene-O—$C_{1-4}$ alkylene;

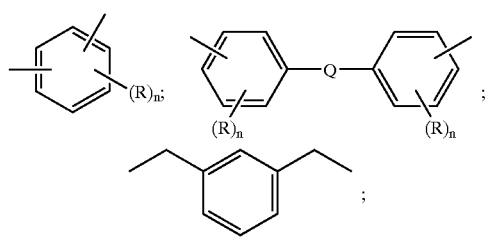

1,5-naphthylene; 2,6-pyridinylene; 1,2-cyclohexylene; 1,3-cyclohexylene; 1,4-cyclohexylene; trans-1,4-cyclohexylene; and trans-5-norbornen-2,3-diyl; wherein n is 0–4; each R is independently selected from the group consisting of $C_{1-4}$ alkyl, $C_{1-4}$ alkoxy, and halogen; and Q is selected from the group consisting of a bond, —$CH_2$—, and —O—.

In Reaction Scheme II a 1H-imidazo compound of Formula IX is reacted with a diisocyanate of Formula X to provide a 1H-imidazo dimer compound of Formula XI, which is a subgenus of Formula I. The reaction can be carried out by adding the diisocyanate to a solution or suspension of a compound of Formula IX in a suitable solvent such as dichloromethane. The reaction can be run at ambient temperature. Many 1H-imidazo compounds of Formula IX are known or can be prepared using known synthetic methods, see for example, U.S. Pat. Nos. 6,069,149; 6,194,425; 6,331,539; 6,451,810; and 6,545,016, European Patent Application 1 104 764, and International Publications WO 02/46188 and WO 02/46194. Many diisocyanates are commercially available; others can be prepared using known synthetic methods. The product or a pharmaceutically acceptable salt thereof can be isolated using conventional methods.

Reaction Scheme II

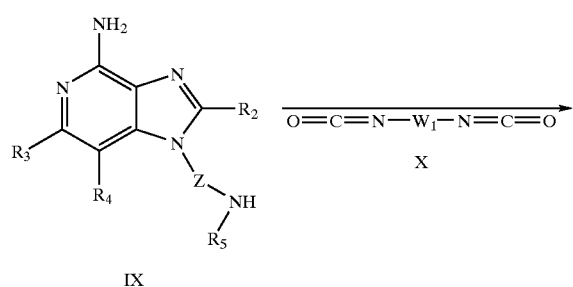

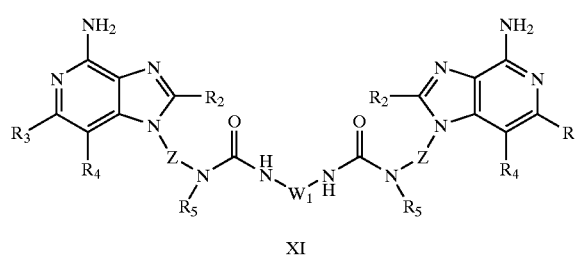

Compounds of the invention can also be prepared according to Reaction Scheme III wherein $R_2$, $R_3$, $R_4$, $R_5$, $W_1$ and Z are as defined above. In Reaction Scheme III a 1H-imidazo compound of Formula IX is reacted with a disulfonyl chloride of Formula XII to provide a 1H-imidazo dimer compound of Formula XIII, which is a subgenus of Formula I. The reaction can be carried out by adding the disulfonyl chloride to a solution or suspension of a compound of Formula IX in a suitable solvent such as dichloromethane in the presence of a base such as triethylamine. The reaction can be run at ambient temperature. Many disulfonyl chlorides are commercially available; others can be prepared using known synthetic methods. The product or a pharmaceutically acceptable salt thereof can be isolated using conventional methods.

Reaction Scheme III

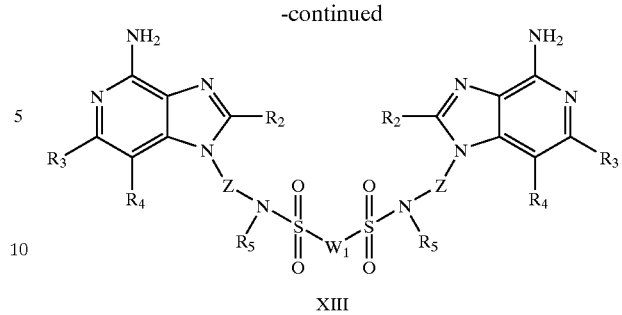

Compounds of the invention can also be prepared according to Reaction Scheme IV wherein $R_2$, $R_3$, $R_4$, $R_5$, $W_1$ and Z are as defined above. In Reaction Scheme IV a 1H-imidazo compound of Formula IX is reacted with a diacid chloride of Formula XIV to provide a 1H-imidazo dimer compound of Formula XV, which is a subgenus of Formula I. The reaction can be carried out by adding the acid chloride to a solution or suspension of a compound of Formula IX in a suitable solvent such as dichloromethane in the presence of a base such as triethylamine. The reaction can be run at ambient temperature. Many diacid chlorides are commercially available; others can be prepared using known synthetic methods. The product or a pharmaceutically acceptable salt thereof can be isolated using conventional methods.

Alternatively, the reaction can be carried out by reacting a compound of Formula IX with a diacid of the formula HOC(O)—$W_1$—C(O)OH using a standard coupling reagent such as 1,3-dicyclohexylcarbodiimide.

Reaction Scheme IV

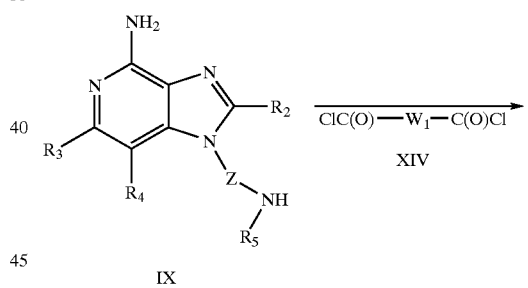

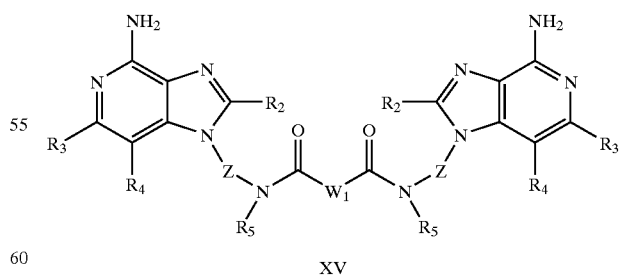

Compounds of the invention can also be prepared according to Reaction Scheme V wherein $R_2$, $R_3$, $R_4$, $R_5$, and Z are as defined above. In Reaction Scheme V a 1H-imidazo compound of Formula IX is reacted with carbonyldiimida zole to provide a 1H-imidazo dimer compound of Formula XVI, which is a subgenus of Formula I. The reaction can be carried out by adding the carbonyldiimidazole to a solution or suspension of a compound of Formula IX in a suitable solvent such as dichloromethane in the presence of a base such as 4-(dimethylamino)pyridine. The reaction can be run at ambient temperature. The product or a pharmaceutically acceptable salt thereof can be isolated using conventional methods.

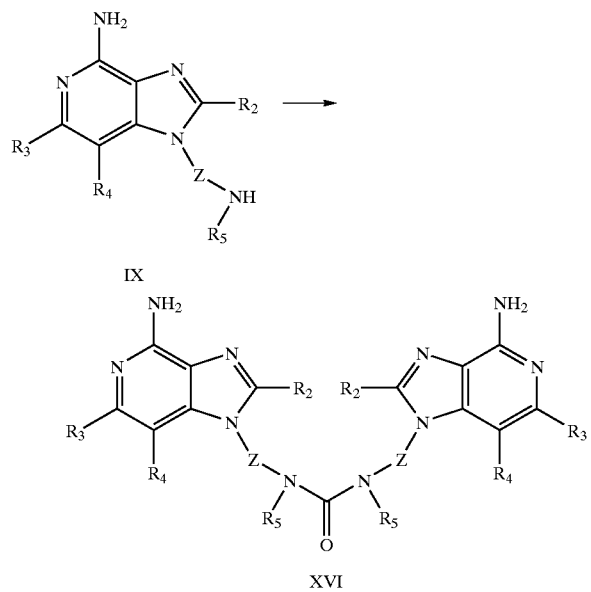

Compounds of the invention can also be prepared according to Reaction Scheme VI wherein $R_2$, $R_3$, $R_4$, $W_1$ and Z are as defined above and BOC is tert-butoxycarbonyl.

In step (1) of Reaction Scheme VI the amino group of a 1H-imidazo compound of Formula XVII is protected with two tert-butoxycarbonyl groups. The reaction can be carried out by treating a solution of a compound of Formula XVII with di-tert-butyl dicarbonate in the presence of a base such as 4-(dimethylamino)pyridine. Many 1H-imidazo compounds of Formula XVII are known or can be prepared using known synthetic methods, see for example, U.S. Pat. Nos. 4,698,338; 4,988,815; 5,175,296; 5,268,376; 5,352,784; 5,389,640; 5,395,937; 5,446,153; 5,741,908; and 6,194,425.

In step (2) of Reaction Scheme VI a protected 1H-imidazo compound of Formula XVIII is reacted with a diisocyanate of Formula X to provide a 1H-imidazo dimer compound of Formula XIX. The reaction can be carried out by adding the diisocyanate to a solution or suspension of a compound of Formula XVIII in a suitable solvent such as dichloromethane. The reaction can be run at ambient temperature.

In step (3) of Reaction Scheme VI the protecting groups are removed by hydrolysis under acidic conditions to provide a 1H-imidazo dimer compound of Formula XX, which is a subgenus of Formula I. The product or a pharmaceutically acceptable salt thereof can be isolated using conventional methods.

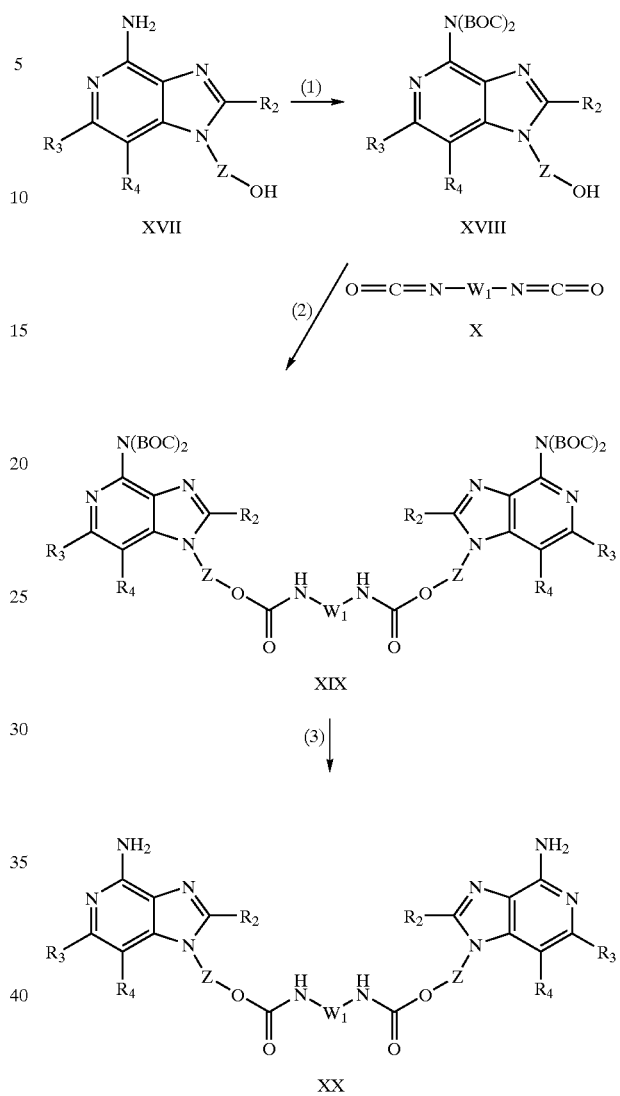

Compounds of the invention can also be prepared according to Reaction Scheme VII wherein $R_2$, $R_3$, $R_4$, $W_1$, Z and BOC are as defined above.

In step (1) of Reaction Scheme VII a protected 1H-imidazo compound of Formula XVIII is reacted with a diacid chloride of Formula XIV to provide a 1H-imidazo dimer compound of Formula XXI. The reaction can be carried out by adding the diacid chloride to a solution or suspension of a compound of Formula XVIII in a suitable solvent such as dichloromethane in the presence of a base such as triethylamine. The reaction can be run at ambient temperature.

In step (2) of Reaction Scheme VII the protecting groups are removed by hydrolysis under acidic conditions to provide a 1H-imidazo dimer compound of Formula XXII, which is a subgenus of Formula I. The product or a pharmaceutically acceptable salt thereof can be isolated using conventional methods.

Reaction Scheme VII

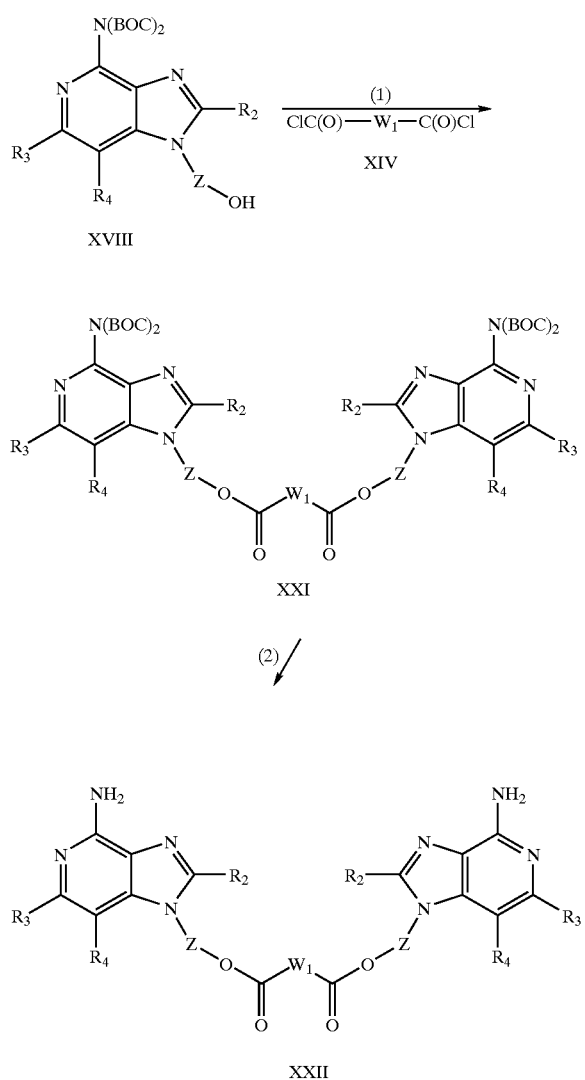

Reaction Scheme VIII

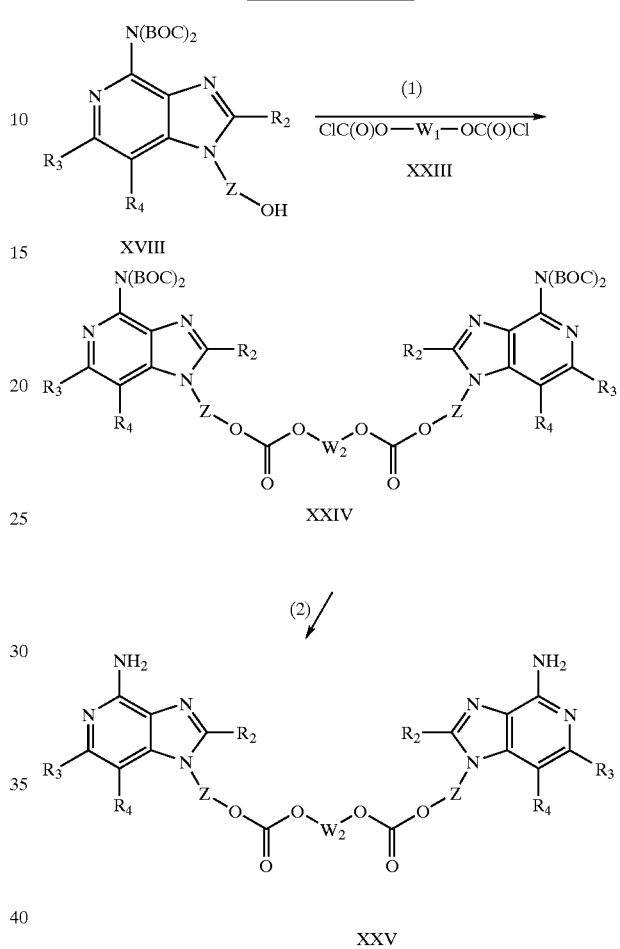

Compounds of the invention can also be prepared according to Reaction Scheme VIII wherein $R_2$, $R_3$, $R_4$, Z and BOC are as defined above and $W_2$ is straight or branched chain $C_{2\text{-}20}$ alkylene.

In step (1) Reaction Scheme VIII a protected 1H-imidazo compound of Formula XVIII is reacted with a compound of Formula XXIII to provide a 1H-imidazo dimer compound of Formula XXIV. The reaction can be carried out by adding a compound of Formula XXIII to a solution or suspension of a compound of Formula XVIII in a suitable solvent such as dichloromethane in the presence of a base such as triethylamine. The reaction can be run at ambient temperature.

In step (2) of Reaction Scheme VIII the protecting groups are removed by hydrolysis under acidic conditions to provide a 1H-imidazo dimer compound of Formula XXV, which is a subgenus of Formula I. The product or a pharmaceutically acceptable salt thereof can be isolated using conventional methods.

Compounds of the invention can also be prepared according to Reaction Scheme IX wherein $R_2$, $R_3$, $R_4$, Z and BOC are as defined above.

In step (1) of Reaction Scheme IX a protected 1H-imidazo compound of Formula XVIII is reacted with carbonyldiimidazole or phosgene to provide a 1H-imidazo dimer compound of Formula XXVI. The reaction can be carried out by adding carbonyldiimidazole or phosgene to a solution or suspension of a compound of Formula XVIII in a suitable solvent such as dichloromethane in the presence of a base such as 4-(dimethylamino)pyridine. The reaction can be run at ambient temperature.

In step (2) of Reaction Scheme IX the protecting groups are removed by hydrolysis under acidic conditions to provide a 1H-imidazo dimer compound of Formula XXVII, which is a subgenus of Formula I. The product or a pharmaceutically acceptable salt thereof can be isolated using conventional methods.

Reaction Scheme IX

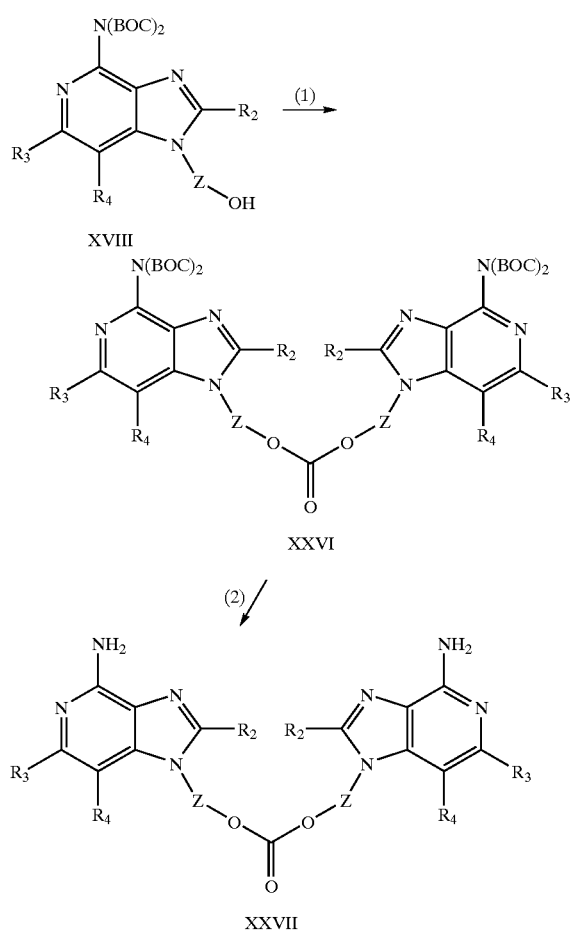

Alternatively, in Reaction Schemes VI–IX when $W_1$ does not contain an alkenylene or alkynylene group, the amine can be protected with benzyloxycarbonyl groups instead of tert-butyoxy carbonyl groups. The protected compound can be prepared by treating a solution of a compound of Formula XVII with dibenzyl dicarbonate or benzyl chloroformate. The protecting groups are later removed by hydrogenolysis.

As used herein, the terms "alkyl", "alkenyl", "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted norbornyl and norbornenyl.

Unless otherwise specified, "alkylene", "alkenylene", and "alkynylene" are the divalent forms of the "alkyl". "alkenyl", and "alkynyl" groups defined above.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

The term "heteroaryl" includes aromatic rings or ring systems that contain at least one ring hetero atom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

"Heterocyclyl" includes non-aromatic rings or ring systems that contain at least one ring hetero atom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, isothiazolidinyl, and imidazolidinyl.

The aryl, heteroaryl, and heterocyclyl groups can be unsubstituted or substituted by one or more substituents independently selected from the group consisting of alkyl, alkenyl, alkoxy, alkylthio, halogen, amino, alkylamino and dialkylamino.

The term "protected —C(O)—" means a carbonyl group that has been converted into another functional group which will stand up to and not interfere with the reaction conditions of the succeeding steps in the synthesis and then can be readily removed. For example, the carbonyl group may be converted to an acyclic ketal, a cyclic ketal or a cyclic dithio ketal. The use of protecting groups is well known and methods for selecting appropriate groups, introducing them into the molecule, and then later removing them have been discussed in for example, Greene, Theodora (1999), *Protective Groups in Organic Synthesis*, John Wiley & Sons, Inc.

Pharmaceutical Compositions and Biological Activity

Pharmaceutical compositions of the invention contain a therapeutically effective amount of a compound of the invention as described above in combination with a pharmaceutically acceptable carrier.

The term "a therapeutically effective amount" or "effective amount" means an amount of the compound sufficient to induce a therapeutic effect, such as cytokine induction, immunomodulation, antitumor activity, and/or antiviral activity. Although the exact amount of active compound used in a pharmaceutical composition of the invention will vary according to factors known to those of skill in the art, such as the physical and chemical nature of the compound, the nature of the carrier, and the intended dosing regimen, it is anticipated that the compositions of the invention will contain sufficient active ingredient to provide a dose of about 100 ng/kg to about 50 mg/kg, preferably about 10 µg/kg to about 5 mg/kg, of the compound to the subject. A variety of dosage forms may be used, such as tablets, lozenges, capsules, parenteral formulations, syrups, creams, ointments, aerosol formulations, transdermal patches, transmucosal patches and the like.

The compounds of the invention can be administered as the single therapeutic agent in the treatment regimen, or the compounds of the invention may be administered in combination with one another or with other active agents, including additional immune response modifiers, antivirals, antibiotics, antibodies, proteins, peptides, oligonucleotides, etc.

The compounds of the invention have been shown to induce the production of certain cytokines in experiments performed according to the tests set forth below. These results indicate that the compounds are useful as immune response modifiers that can modulate the immune response in a number of different ways, rendering them useful in the treatment of a variety of disorders.

Cytokines whose production may be induced by the administration of compounds according to the invention generally include interferon-α (IFN-α) and/or tumor necrosis factor-α (TNF-α) as well as certain interleukins (IL). Cytokines whose biosynthesis may be induced by compounds of the invention include IFN-α, TNF-α, IL-1, IL-6, IL-10 and IL-12, and a variety of other cytokines. Among other effects, these and other cytokines can inhibit virus production and tumor cell growth, making the compounds useful in the treatment of viral diseases and neoplastic diseases. Accordingly, the invention provides a method of inducing cytokine biosynthesis in an animal comprising administering an effective amount of a compound or composition of the invention to the animal. The animal to which the compound or composition is administered for induction of cytokine biosynthesis may have a disease as described infra, for example a viral disease or a neoplastic disease, and administration of the compound may provide therapeutic treatment. Alternatively, the compound may be administered to the animal prior to the animal acquiring the disease so that administration of the compound may provide a prophylactic treatment.

In addition to the ability to induce the production of cytokines, the compounds of the invention affect other aspects of the innate immune response. For example, natural killer cell activity may be stimulated, an effect that may be due to cytokine induction. The compounds may also activate macrophages, which in turn stimulate secretion of nitric oxide and the production of additional cytokines. Further, the compounds may cause proliferation and differentiation of B-lymphocytes.

Compounds of the invention also have an effect on the acquired immune response. For example, the production of the T helper type 1 (Th1) cytokine IFN-γ is induced indirectly and the production of the T helper type 2 (Th2) cytokines IL-4, IL-5 and IL-13 are inhibited upon administration of the compounds.

Whether for prophylaxis or therapeutic treatment of a disease, and whether for effecting innate or acquired immunity, the compound or composition may be administered alone or in combination with one or more active components as in, for example, a vaccine adjuvant. When administered with other components, the compound and other component or components may be administered separately; together but independently such as in a solution; or together and associated with one another such as (a) covalently linked or (b) non-covalently associated, e.g., in a colloidal suspension.

Diseases for which IRMs identified herein may be used as treatments include, but are not limited to:

(a) viral diseases, such as genital warts, common warts, plantar warts, hepatitis B, hepatitis C, herpes simplex virus type I and type II, molluscum contagiosum, variola, HIV, CMV, VZV, rhinovirus, adenovirus, coronavirus, influenza, para-influenza;

(b) bacterial diseases, such as tuberculosis, and mycobacterium avium, leprosy;

(c) other infectious diseases, such as fungal diseases, chlamydia, candida, aspergillus, cryptococcal meningitis, pneumocystis carnii, cryptosporidiosis, histoplasmosis, toxoplasmosis, trypanosome infection, leishmaniasis;

(d) neoplastic diseases, such as initraepithelial neoplasias, cervical dysplasia, actinic keratosis, basal cell carcinoma, squamous cell carcinoma, hairy cell leukemia, Karposi's sarcoma, melanoma, renal cell carcinoma, myelogeous leukemia, multiple myeloma, non-Hodgkin's lymphoma, cutaneous T-cell lymphoma, and other cancers;

(e) Th2 mediated, atopic, and autoimmune diseases, such as atopic dermatitis or eczema, eosinophilia, asthma, allergy, allergic rhinitis, systemic lupus erythematosis, essential thrombocythaemia, multiple sclerosis, Ommen's syndrome, discoid lupus, alopecia areata, inhibition of keloid formation and other types of scarring, and enhancing would healing, including chronic wounds; and (f) as a vaccine adjuvant for use in conjunction with any material that raises either humoral and/or cell mediated immune response, such live viral and bacterial immunogens and inactivated viral, tumor-derived, protozoal, organism-derived, fungal, and bacterial immunogens, toxoids, toxins, polysaccharides, proteins, glycoproteins, peptides, cellular vaccines, DNA vaccines, recombinant proteins, glycoproteins, and peptides, and the like, for use in connection with, e.g., BCG, cholera, plague, typhoid, hepatitis A, B, and C, influenza A and B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, and yellow fever.

IRMs may also be particularly helpful in individuals having compromised immune function. For example, IRM compounds may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need there of (having the disease) by administering a therapeutically effective amount of a compound or salt of formula (I) to the animal.

An amount of a compound effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased over the background level of such cytokines. The precise amount will vary according to factors known in the art but is expected to be a dose of about 100 ng/kg to about 50 mg/kg, preferably about 10 µg/kg to about 5 mg/kg. The invention also provides a method of treating a viral infection in an animal and a method of treating a neoplastic disease in an animal comprising administering an effective amount of a compound or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg.

The invention is further described by the following examples, which are provided for illustration only and are not intended to be limiting in any way.

EXAMPLE 1

N,N'-bis[4-(4-amino-2-butyl-1H-imidazo[4,5-c]quinolin-1-yl)butyl]urea

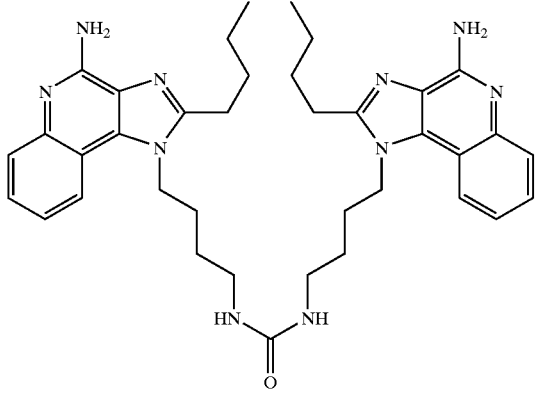

A suspension of 1-(4-aminobutyl)-2-butyl-1H-imidazo[4,5-c]quinolin-4-amine (267 mg, 0.859 mmol) in 10 mL of $CH_2Cl_2$ was treated with carbonyldiimidazole (71 mg, 0.438 mmol) and stirred under $N_2$ overnight. The reaction mixture was then treated with 2 mg of 4-(dimethylamino)pyridine and stirred an additional 3 days (d). The reaction mixture was then concentrated under reduced pressure and the resulting white solid was triturated with $H_2O$ and filtered. The resulting solid was purified by column chromatography ($SiO_2$, 10–20% $MeOH/CHCl_3$) to give a white solid. Crystallization from propyl acetate/MeOH gave the desired product (168 mg). M. p. 218.1–219.7° C.;

$^1H$ NMR (300 MHz, DMSO-$d_6$) δ 7.98 (d, J=7.8 Hz, 2H), 7.60 (d, J=8.3 Hz, 2H), 7.39 (t, J=7.1 Hz, 2H), 7.23 (t, J=7.0 Hz, 2H), 6.48 (s, 4H), 5.81 (t, J=5.6 Hz, 2H) 4.47 (t, J=7.3 Hz, 4H), 3.02 (q, J=6.2 Hz, 4H), 2.89 (t, J=7.7 Hz, 4H), 1.82–1.72 (m, 8H), 1.58–1.37 (m, 8H), 0.93 (t, J=7.3 Hz, 6H);

MS 649 (M+H)$^+$;

Anal calcd for $C_{37}H_{48}N_{10}O \cdot 0.87H_2O$: % C, 66.88; % H, 7.54; % N, 21.08. Found: % C, 66.92; % H, 7.57; % N, 20.92.

Karl Fisher titration 2.36% $H_2O$.

EXAMPLE 2

N,N''-1,3-phenylenebis{N'-[4-(4-amino-2-butyl-1H-imidazo[4,5-c]quinolin-1-yl)butyl]urea}

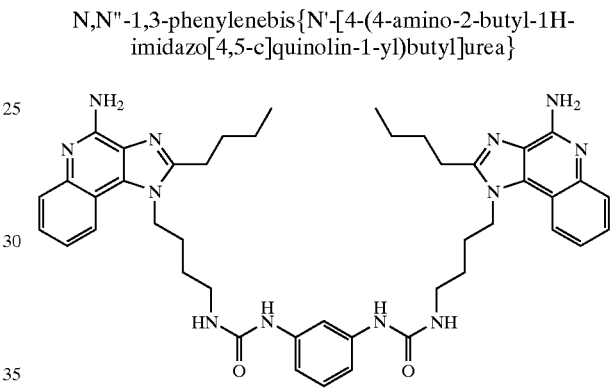

A suspension of 1-(4-aminobutyl)-2-butyl-1H-imidazo[4,5-c]quinolin-4-amine (3.11 g, 10.0 mmol) in 100 mL of $CH_2Cl_2$ was treated with 1,3-phenylene diisocyanate (800 mg, 5.0 mmol) and stirred under $N_2$ overnight. The reaction mixture was then concentrated under reduced pressure to give a white solid. The white solid was then dissolved in 150 mL of hot 15% $MeOH/CHCl_3$. After slow evaporation of the solvent, a white precipitate had formed. The solid was isolated by filtration, washed with 10% $MeOH/CHCl_3$ (3×10 mL) and dried under vacuum to give the desired product (400 mg) as a white powder. M. p. 160.3–165.6° C.; $^1H$ NMR (300 MHz, DMSO-$d_6$) δ 8.34 (s, 2H), 8.01 (d, J=7.9 Hz, 2H), 7.60 (d, J=8.3 Hz, 2H), 7.43 (s, 1H), 7.38 (t, J=7.6 Hz, 2H), 7.22 (t, J=7.0 Hz, 2H), 7.05–6.94 (m, 3H), 6.45 (s, 4H), 6.07 (t, J=5.4 Hz, 2H) 4.53 (t, J=7.4 Hz, 4H), 3.15 (m, 4H), 2.92 (t, J=7.7 Hz, 4H), 1.88–1.74 (m, 8H), 1.66 (m, 4H), 1.43 (m, 4H), 0.92 (t, J=7.3 Hz, 6H);

$^{13}C$ NMR (75 MHz, DMSO-$d_6$) δ 155.6, 153.4, 152.1, 145.1, 141.2, 132.6, 129.0, 126.8, 126.7, 126.6, 121.5, 120.3, 115.2, 111.0, 107.3, 45.0, 38.9, 30.1, 27.6, 27.2, 26.5, 22.3, 14.1; Anal calcd for $C_{44}H_{54}N_{12}O_2 \cdot 2.72H_2O$: % C, 63.52; % H, 7.20; % N, 20.20. Found % C, 63.29; % H, 7.19; % N, 20.16.

Karl Fisher titration 5.88% $H_2O$.

EXAMPLE 3

N-[4-(4-amino-2-butyl-1H-imidazo[4,5-c]quinolin-1-yl)butyl]-N'-(4-{4-[({[4-(4-amino-2-butyl-1H-imidazo[4,5-c]quinolin-1-yl)butyl]amino}carbonyl)amino]phenoxy}phenyl)urea

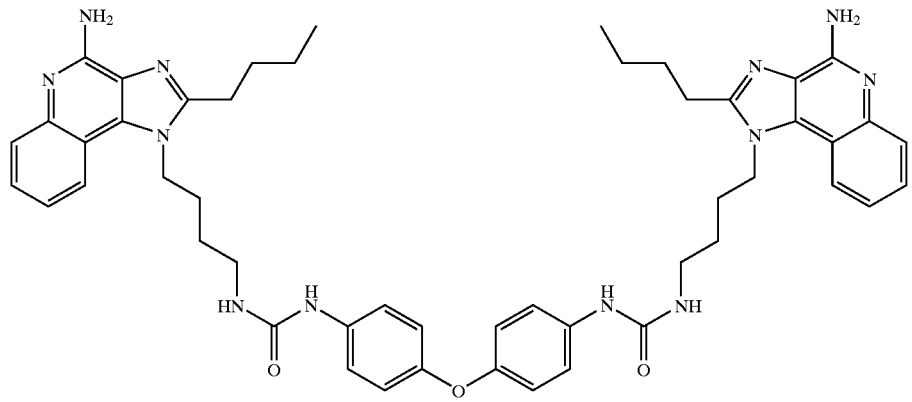

A suspension of 1-(4-aminobutyl)-2-butyl-1H-imidazo[4,5-c]quinolin-4-amine (3.11 g, 10.0 mmol) in 100 mL of $CH_2Cl_2$ was treated with 4,4'-oxybisphenyl isocyanate) (1.26 g, 5.0 mmol) and stirred under $N_2$ for 2 d. The reaction mixture was then filtered and the resulting solid was washed with $Et_2O$ to give 3.97 g of a white solid. The white solid was then treated with 100 mL of hot pyridine and filtered to remove the insoluble material. The filtrate was then concentrated under reduced pressure and the residue was dissolved in 50 mL of hot pyridine. After several days, a crystalline product formed. The crystals were isolated by filtration and dried under vacuum at 55° C. for 3 d to give the desired product (2.5 g). M. p. 152.1–156.1° C.;

$^1$H NMR (300 MHz, DMSO-$d_6$) δ 8.36 (s, 2H), 8.02 (d, J=8.1 Hz, 2H), 7.61 (d, J=8.2 Hz, 2H), 7.39 (t, J=7.5 Hz, 2H), 7.34 (d, J=9.0 Hz, 4H), 7.22 (t, J=7.9 Hz, 2H), 6.84 (d, J=8.9 Hz, 4H), 6.45 (s, 4H), 6.10 (t, J=6.0 Hz, 2H), 4.53 (t, J=7.3 Hz, 4H), 3.15 (q, J=6.0 Hz, 4H), 2.92 (t, J=7.7 Hz, 4H), 1.90–1.74 (m, 8H), 1.60 (m, 4H), 1.44 (m, 4H), 0.93 (t, J=7.3 Hz, 6H);

$^{13}$C N (75 MHz, DMSO-$d_6$) δ 155.3, 152.9, 151.6, 151.2, 144.6, 135.9, 132.1, 126.3, 126.2, 126.1, 121.1, 119.8, 119.2, 118.5, 114.7, 44.5, 38.9, 29.6, 27.2, 26.8, 26.1, 21.9, 13.7; Anal calcd for $C_{50}H_{58}N_{12}O_3 \cdot 0.24H_2O$: % C, 68.29; % H, 6.70; % N, 19.11. Found: % C, 68.11; % H, 6.70; % N, 19.17.

Karl Fisher titration 0.49% $H_2O$.

EXAMPLE 4

N,N''-trans-1,4-cyclohexylenebis{N'-[4-(4-amino-2-butyl-1H-imidazo[4,5-c]quinolin-1-yl)butyl]urea}

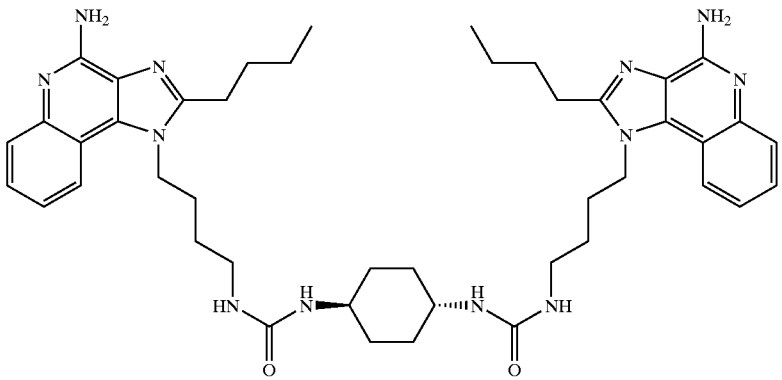

A suspension of 1-(4-aminobutyl)-2-butyl-1H-imidazo[4,5-c]quinolin-4-amine (3.11 g, 10.0 mmol) in 100 mL of $CH_2Cl_2$ was treated with trans-1,4-cyclohexylene diisocyanate (831 mg, 5.0 mmol) and stirred under $N_2$ for 3 d. The reaction mixture was then filtered and the resulting solid was washed with $Et_2O$ to give a white solid. The white solid was then triturated with hot MeOH and filtered to give a white solid. The solid was then dissolved in 150 mL of hot 15% MeOH/$CHCl_3$. After slow evaporation of the solvent, a white precipitate had formed. The solid was isolated by filtration and then dissolved in a minimum amount of hot pyridine. The resulting crystals were isolated by filtration and dried under vacuum at 55° C. for 3 d to give the desired product (1.45 g). M. p. 184.5–188.8° C.;

$^1$H NMR (300 MHz, DMSO-$d_6$) δ 8.00 (d, J=8.0 Hz, 2H), 7.61 (d, J=8.1 Hz, 2H), 7.41 (t, J=7.4 Hz, 2H), 7.24 (t, J=7.2

Hz, 2H), 6.45 (s, 4H), 5.70 (t, J=5.2 Hz, 2H), 5.62 (d, J=7.8 Hz, 2H), 4.50 (m, 4H), 3.25 (m, 2H), 3.03 (m, 4H), 2.91 (t, J=7.7 Hz, 4H), 1.87–1.70 (m, 12H), 1.53–1.39 (m, 8H), 1.05 (m, 4H), 0.96 (t, J=7.3 Hz, 6H);

$^{13}$C NMR (125 MHz, DMSO-d$_6$) δ 157.4, 152.9, 151.6, 144.6, 132.1, 126.3, 126.2, 126.1, 121.0, 119.8, 114.7, 47.5, 44.5, 38.5, 31.9, 29.6, 27.2, 27.1, 26.1, 21.9, 13.7;

Anal calcd for $C_{44}H_{60}N_{12}O_2 \cdot 1.43H_2O$: % C, 64.86; % H, 7.78; % N, 20.63. Found: C, % 64.79; % H, 7.92; % N, 20.44.

Karl Fisher titration 3.17% $H_2O$.

EXAMPLE 5

N,N'-bis(2-{2-[4-amino-2-(2-methoxyethyl)-1H-imidazo[4,5-c]quinolin-1-yl]ethoxy}ethyl)benzene-1,3-disulfonamide

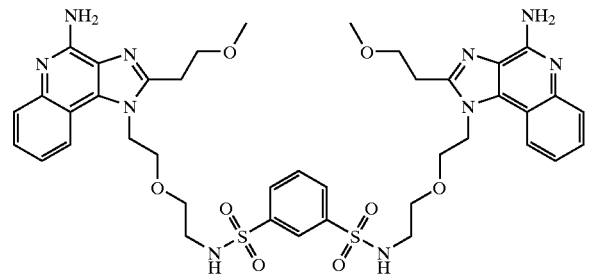

A solution of 1-[2-(2-aminoethoxy)ethyl]-2-(2-methoxyethyl)-1H-imidazo[4,5-c]quinotin-4-amine (500 mg, 1.52 mmol) in 15 mL of $CH_2Cl_2$ was treated with triethylamine (417 μl, 3.04 mmol) and 1,3-benzenedisulfonyl chloride (209 mg, 0.75 mmol) and stirred under $N_2$ overnight. The reaction mixture was then treated with saturated NaHCO$_3$ solution, 50 mL of $CH_2Cl_2$ and 5 mL of MeOH. The layers were separated and the organic portion was washed with $H_2O$ and brine. The organic portion was then dried over $Na_2SO_4$ and concentrated. Column chromatography (SiO$_2$, 8% MeOH/CHCl$_3$ saturated with NH$_4$H) gave the product (155 mg) as an off-white foam. M. p. 115–120° C.;

$^1$H NMR (300 MHz, DMSO-d$_6$) δ 8.15 (t, J=1.6 Hz, 1H), 8.01–7.94 (m, 6H), 7.73 (t, J=7.7 Hz, 1H), 7.60 (dd, J=1.1, 8.3 Hz, 2H), 7.40 (ddd, J=1.1, 7.2, 8.1 Hz, 2H), 7.20 (ddd, J=1.2, 7.0, 8.2 Hz, 2H), 6.46 (s, 4H), 4.68 (t, J=5.3 Hz, 4H), 3.79 (t, J=6.8 Hz, 4H), 3.75 (t, J=5.2 Hz, 4H), 3.28 (m, 4H), 3.26 (s, 6H), 3.17 (t, J=6.8 Hz, 4H, 2.68 (m, 4H), $^{13}$C NMR (75 MHz, DMSO-d$_6$) δ 152.0, 151.9, 145.1, 142.0, 132.6, 131.0, 130.3, 126.7, 124.6, 121.4, 120.4, 115.1, 70.5, 69.6, 69.2, 58.4, 45.3, 42.5, 27.6.

Anal calcd for $C_{40}H_{48}N_{10}O_8S_2 \cdot 0.62H_2O$: % C, 55.08; % H, 5.69; % N, 16.06. Found: % C, 55.13; % H, 5.62; % N, 15.82.

Karl Fisher titration 1.29% $H_2O$.

EXAMPLE 6

N,N'-bis(2-{2-[4-amino-2-(2-methoxyethyl)-1H-imidazo[4,5-c]quinolin-1-yl]ethoxy}ethyl) terephthalamide

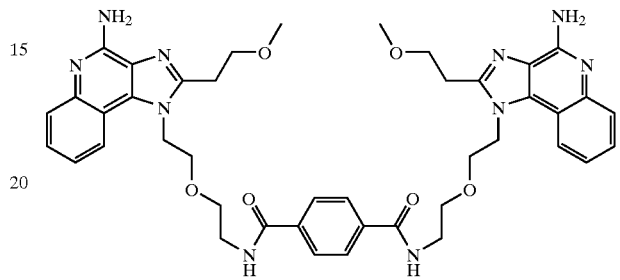

A solution of 1-[2-(2-aminoethoxy)ethyl]-2-(2-methoxyethyl)-1H-imidazo[4,5-c]quinolin-4-amine (500 mg, 1.52 mmol) in 15 mL of $CH_2Cl_2$ was treated with triethylamine (417 μl, 3.04 mmol) and terephthaloyl chloride (152 mg, 0.75 mmol) and stirred under $N_2$ overnight. The reaction mixture was then treated with saturated NaHCO$_3$ solution, 50 mL of $CH_2Cl_2$ and 5 mL of MeOH. The layers were separated and the organic portion was washed with $H_2O$ and brine. The organic portion was then dried over $Na_2SO_4$ and concentrated. Column chromatography (SiO$_2$, 5% MeOH/CHCl$_3$ saturated with NH$_4$OH) gave the product as an off-white foam. The material was crystallized from isopropanol to give the desired product (160 mg). M. p. 229–233° C.;

$^1$H NMR (300 MHz, DMSO$_6$) δ 8.47 (t, J=5.4 Hz, 2H), 8.05 (d, J=7.8 Hz, 2H), 7.82 (s, 4H), 7.61 (dd, J=1.1, 8.3 Hz, 2H), 7.40 (ddd, J=1.1, 7.2, 8.1 Hz, 2H), 7.19 (ddd, J=1.2, 6.9, 8.2 Hz, 2H), 6.50 (s, 4H), 4.76 (t, J=4.9 Hz, 4H), 3.90 (t, J=5.0 Hz, 4H), 3.78 (t, J=6.8 Hz, 4H), 3.49 (t, J=5.7 Hz, 4H), 3.38 (t, J=5.3 Hz, 4H), 3.33 (s, 6H), 3.20 (t, J=6.8 Hz, 4H);

$^{13}$C NMR (75 MHz, DMSO-d$_6$) δ 166.1, 152.0, 151.9, 145.1, 136.9, 132.7, 127.4, 126.7, 121.4, 120.5, 115.1, 70.4, 69.4, 69.2, 58.4, 45.8, 27.6.

Anal calcd for $C_{42}H_{48}N_{10}O_6 \cdot 0.44H_2O$: % C, 63.31; % H, 6.18; N, % 17.58. Found: % C, 63.01; % H, 6.25; % N, 17.58.

Karl Fisher titration 0.99% $H_2O$.

EXAMPLE 7

N,N''-1,8-octanediylbis[N'-(2-{2-[4-amino-2-(methoxyethyl)-1H-imidazo[4,5-c]quinolin-1-yl]ethoxy}ethyl)urea]

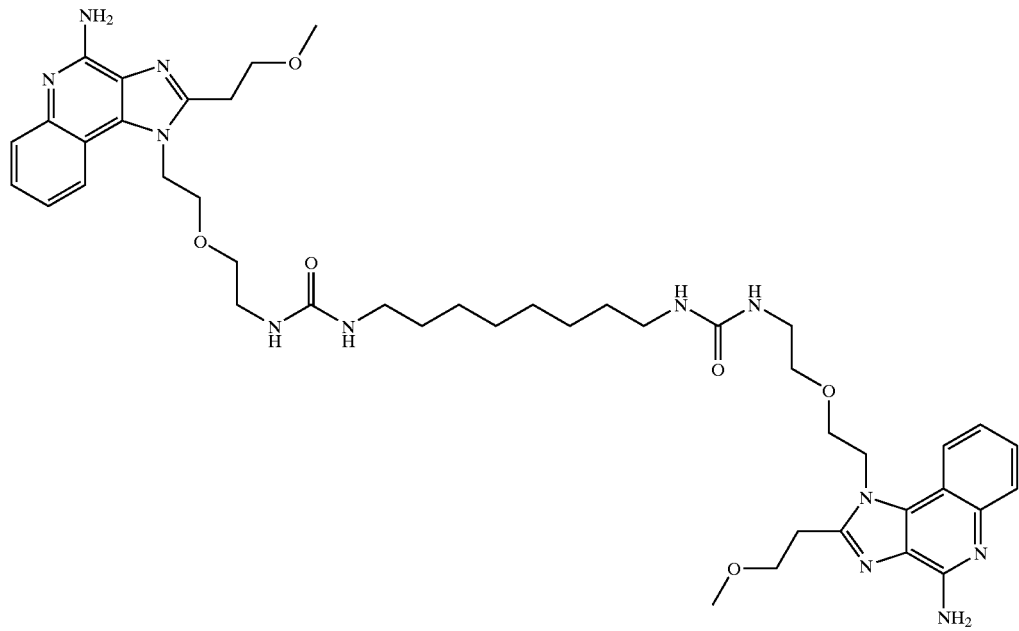

A solution of 1-[2-(2-aminoethoxy)ethyl]-2-(2-methoxyethyl)-1H-imidazo[4,5-c]quinolin-4-amine (500 mg, 1.52 mmol) in 25 mL of CH$_2$Cl$_2$ was treated with 1,8-diisocyanatooctane (148 μL, 0.76 mmol) and stirred under N$_2$ overnight. The reaction mixture was then concentrated under reduced pressure to give a tan foam. Column chromatography (SiO$_2$, 5–10% MeOH/CHCl$_3$) yielded 570 mg of a mauve colored foam. This was dissolved in 10 mL of hot MeOH and treated with 1 g of decolorizing charcoal. The hot solution was filtered through a; pad of Celite® filter agent and the filtrate was concentrated to give the desired product (245 mg) as a white powder. M. p. 172.5–177.0° C.

$^1$H NMR (300 MHz, DMSO-d$_6$) δ 8.04 (d, J=8.0Hz, 2H), 7.61 (d, J=7.5Hz, 2H), 7.41 (t, J=7.2 Hz, 2H), 7.23 (t, J=7.1 Hz, 2H), 6.48 (s, 4H), 5.82 (t, J=5.5 Hz, 2H), 5.70 (t, J=5.6 Hz, 2H), 4.73 (t, J=5.0 Hz, 4H); 3.85–3.80 (m, 8H), 3.29 (s, 6H), 3.21 (t, J=6.8 Hz, 4H), 3.05 (q, J=5.6 Hz, 4H), 2.92 (q, J=5.9 Hz, 4H), 1.31 (m, 4H), 1.21 (br s, 8H);

$^{13}$C NMR (75 MHz, DMSO-d$_6$) δ 157.0, 150.7, 150.6, 143.8, 131.4, 125.4, 125.3, 120.2, 119.1, 113.4, 69.5, 69.2, 67.9, 57.2, 44.2, 29.1, 27.9, 26.3, 25.4.

Anal calcd for C$_{44}$H$_{62}$N$_{12}$O$_6$·0.74H$_2$O: % C, 60.86; % H, 7.37; % N, 19.36. Found: % C, 60.87; % H, 7.36; % N, 19.19.

Karl Fisher titration 1.53% H$_2$O.

EXAMPLE 8

1-[10-(4-amino-2-ethoxymethyl-1H-imidazo[4,5-c]quinolin-1-yl)decyl]-2-ethoxymethyl-1H-imidazo[4,5-c]quinoline-4-amine

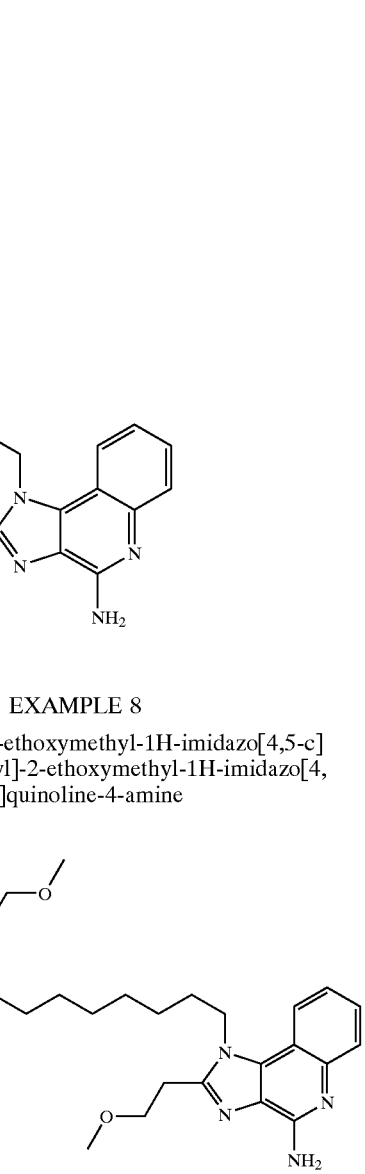

Part A

A solution of 4-chloro-3-nitroquinoline (2.50 g, 12.2 mmol) in 75 mL of dry CH$_2$Cl$_2$ was treated with triethylamine (3.40 mL, 24.4 mmol) and 1,10-diaminodecane (1.05 g, 6.1 mmol) and the reaction mixture was stirred under N$_2$ overnight. The reaction mixture was then concentrated under reduced pressure and the resulting yellow solid was triturated with hot H$_2$O (100 mL). Filtration gave a yellow solid which was then subjected to column chromatography (SiO$_2$, 0–5% MeOH/CHCl$_3$) to give N,N'-bis(3-nitroquinolin-4-yl)decane-1,10-diamine (1.90 g) as a yellow foam.

Part B

The material from Part A (1.90 g) was dissolved in 100 mL of MeOH and treated with 5% Pt/C. The reaction mixture was shaken under an atmosphere of H₂ (50 psi; 3.4×10⁵ Pa) overnight. The reaction mixture was then purged with N₂ and filtered through a pad of Celite® filter agent. The filtrate was concentrated to give N,N'-bis(3-aminoquinolin-4-yl)decane-1,10-diamine (0.81 g) as a yellow syrup.

Part C

The material from Part B (810 mg, 1.78 mmol) was dissolved in 20 mL of dry CH₂Cl₂ and treated with triethylamine (544 μL, 3.91 mmol) and ethoxyacetyl chloride (429 μL, 3.91 mmol) and the reaction mixture was stirred under N₂ for 2 h. The reaction mixture was then concentrated under reduced pressure and the resulting syrup was dissolved in 20 mL of ethanol and treated with 1.5 mL of triethylamine. The reaction mixture was refluxed overnight and then concentrated under reduced pressure. The resulting material was partitioned between 100 mL of CH₂Cl₂ and H₂O. The layers were separated and the organic portion was washed with H₂O (2×) and brine, dried over Na₂SO₄ and concentrated. Column chromatography (SiO₂, 5% MeOH/CHCl₃) gave 2-(ethoxymethyl)-1-{10-[2-(ethoxymethyl)-1H-imidazo[4,5-c]quinolin-1-yl]decyl}-1H-imidazo[4,5-c]quinoline (490 mg) as a light yellow solid.

Part D

The material from Part C (490 mg, 0.828 mmol) was dissolved in 10 mL of CH₂Cl₂ and treated with 3-chloroperoxybenzoic acid (77% max., 407 mg, 1.82 mmol). After stirring overnight, an additional 40 mg of 3-chloroperoxybenzoic acid was added. Stirring was continued for 4 h, then the reaction mixture was diluted with 50 mL of CH₂Cl₂ and washed with 1% Na₂CO₃ solution (2×), H₂O, and brine. The organic portion was dried over Na₂SO₄ and concentrated to give 2-(ethoxymethyl)-1-{10-[2-(ethoxymethyl)-5-oxido-1H-imidazo[4,5-c]quinolin-1-yl]decyl}-1H-imidazo[4,5-c]quinoline 5-oxide (463 mg) as an off-white powder.

Part E

The material from Part D (463 mg, 0.741 mmol) was dissolved in 20 mL of CH₂Cl₂ and treated with 2 mL of concentrated NH₄OH solution. The solution was stirred rapidly and tosyl chloride (310 mg) was added in two portions. After stirring for 30 min, the reaction mixture was diluted with 20 mL of CH₂Cl₂ and washed with H₂O, 1% Na₂CO₃ solution (3×), H₂O, and brine. The organic portion was dried over Na₂SO₄ and concentrated to give a tan powder. Column chromatography (SiO₂, 2.5–3.5% MeOH/CHCl₃) yielded 362 mg of the desired product as a cream-colored foam. M. p. 237–238° C.;

¹H NMR (300 MHz, CDCl₃) δ 7.95 (dd, J=1.0, 8.2 Hz, 2H), 7.82 (dd, J=1.1, 8.5 Hz, 2H), 7.52 (ddd, J=1.3, 7.0, 8.5 Hz, 2H), 7.32 (ddd, J=1.3, 7.1, 8.5 Hz, 2H), 5.38 (s, 4H), 4.80 (s, 4H), 4.55 (t, J=7.9 Hz, 4H), 3.60 (q, J=7.0 Hz, 4H), 1.98 (m, 4H),1.49 (m, 4H), 1.33 (m, 8H), 1.24 (t, J=7.0 Hz, 6H);

¹³C NMR (75 MHz, 10% CD₃OD/CDCl₃) δ 151.5, 149.0, 144.7, 134.4, 127.8, 126.7, 126.2, 122.6, 120.0, 115.1, 66.4, 65.0, 46.5, 30.3, 29.4, 29.3, 26.8, 15.1;

Anal calcd for C₃₆H₄₆N₈O₂·0.40H₂O: % C, 68.63; % H, 7.49; % N, 17.79. Found: % C, 68.49; % H, 7.54; % N, 17.82.

EXAMPLES 9–16

Using the general method of Example 5,4-amino-1-[2-(4-piperidyl)ethyl]-1H-imidazo[4,5-c]quinoline (Example 113 in EP 1 104 764) can be reacted with a disulfonyl chloride from the table below to provide a dimer of the invention. All of the disulfonyl chlorides in the table are commercially available.

| Example | Disulfonyl Chloride | W₁ |
|---|---|---|
| 9 | 4,4'-Biphenyldisulfonyl chloride | 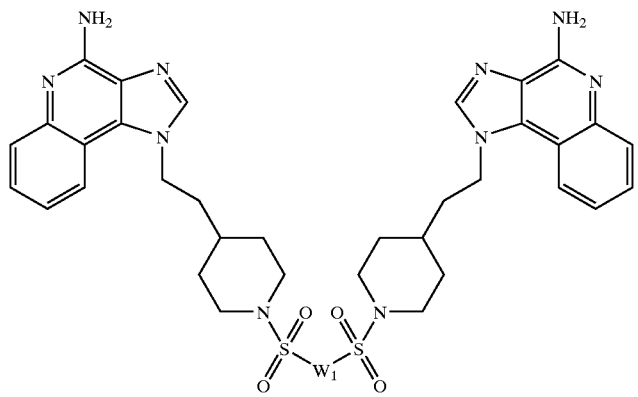 |
| 10 | 2,4-Mesitylenedisulfonyl dichloride | |

-continued
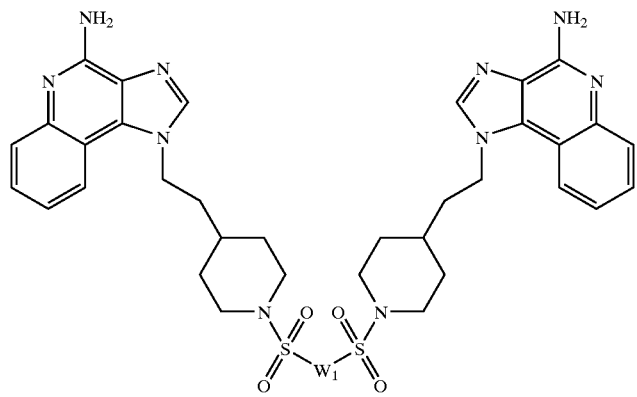
| Example | Disulfonyl Chloride | $W_1$ |
|---|---|---|
| 11 | 4,4'-Methylene-bis(benzenesulfonylchloride) | 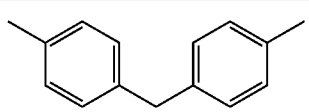 |
| 12 | 4,4'-Bis(chlorosulfonyl)diphenylether | 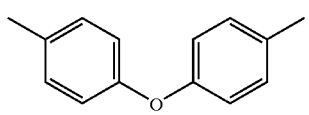 |
| 13 | 1,4-Butanedisulfonylchloride | —(CH$_2$)$_4$— |
| 14 | 1,3-Benzenedisulfonyl chloride | 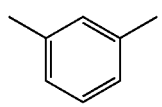 |
| 15 | 1,2-Benzenedisulfonyl chloride | 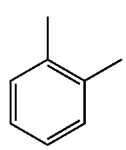 |
| 16 | 1,4-Bis(chlorosulfonyl)octafluorobutane | —(CF$_2$)$_4$— |

EXAMPLES 17–35

Using the general method of Example 2, 1-(2-amino-2-methylpropyl)-2-(ethoxymethyl)-1H-imidazo[4,5-c]quinolin-4-amine can be reacted with a diisocyanate from the table below to provide a dimer of the invention. All of the diisocyanates in the table are commercially available.

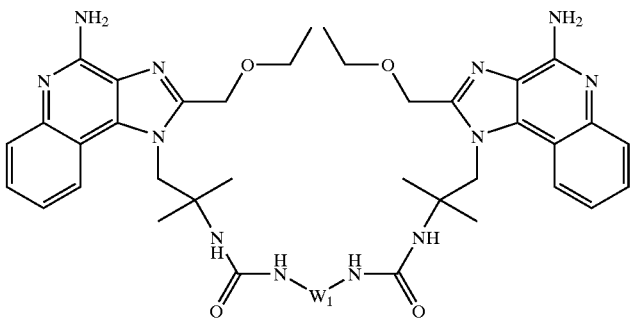

| Example | Diisocyanate | $W_1$ |
|---|---|---|
| 17 | Tolylene 2,6-diisocyanate | |
| 18 | 1,4-Phenylene diisocyanate | |
| 19 | Hexamethylene diisocyanate | $-(CH_2)_6-$ |
| 20 | 3,3'-Bianisole-4,4'-isocyanic acid ester | |
| 21 | Dicyclohexylmethane-4,4'-diisocyanate | |
| 22 | 3,3'-Bitolyene-4,4'-diisocyanate | |
| 23 | 4,4'-Diisocyanato-3,3'-dimethyldiphenylmethane | |
| 24 | m-Xylene diisocyanate | |

-continued

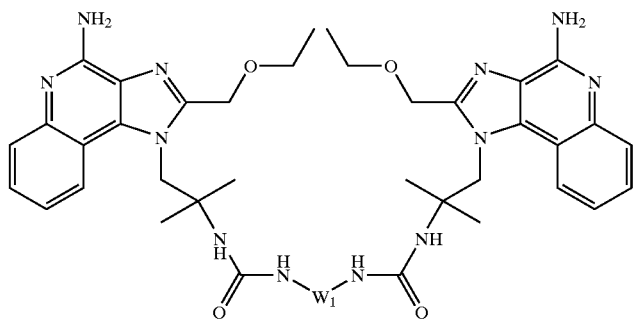

| Example | Diisocyanate | W₁ |
|---|---|---|
| 25 | 4,4'-Diphenylmethane diisocyanate | 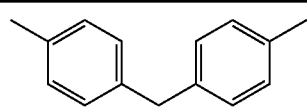 |
| 26 | 1,2-Diisocyanatododecane | —(CH$_2$)$_{12}$— |
| 27 | 4,4'-Methylenebis(2-chlorophenyl isocyanate) | 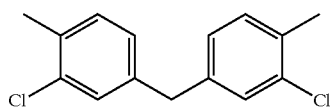 |
| 28 | 1,5-Naphthalenediisocyanate | 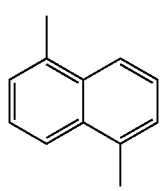 |
| 29 | 3,3'-Dichlorodiphenyl 4,4'-diisocyanate | 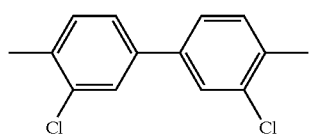 |
| 30 | 1,4-Diisocyanatobutane | —(CH$_2$)$_4$— |
| 31 | 1,3-Bis(isocyanatomethyl)cyclohexane | 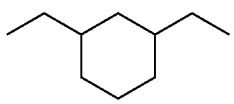 |
| 32 | 3,3',5,5'-Tetraethyldiphenylmethane-4,4'-diisocyanate | 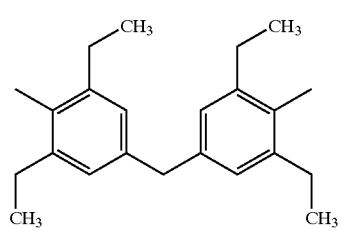 |
| 33 | 1,8-Diisocyanatooctane | —(CH$_2$)$_8$— |
| 34 | 2,4,6-Trimethyl-1,3-phenylene diisocyanate | 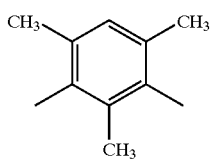 |

-continued

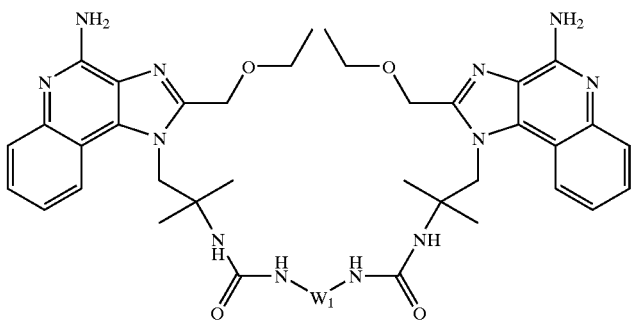

| Example | Diisocyanate | $W_1$ |
|---|---|---|
| 35 | 2,4'-Methylenebis(phenyl isocyanate) | 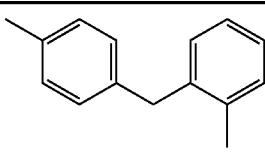 |

EXAMPLES 36–56

Using the general method of Example 6, 1-(4-aminobutyl)-6,7,8,9-tetrahydro-2-methoxyethyl)-1H-imidazo[4,5-c]quinolin-4-amine (Example 172 Part A in U.S. Pat. No. 6,451,810) can be reacted with a diacid dichloride from the table below to provide a dimer of the invention. All of the diacid dichlorides in the table are commercially available.

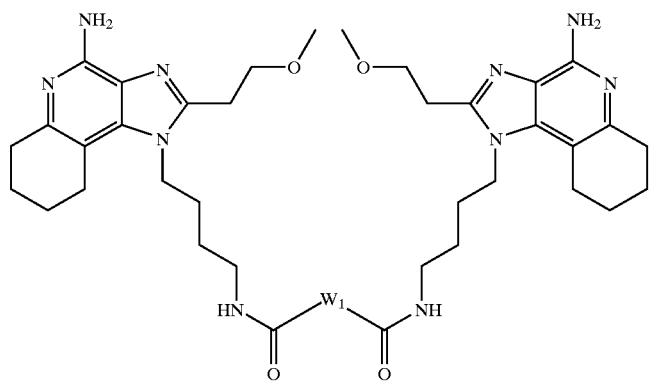

| Example | Diacid Dichloride | $W_1$ |
|---|---|---|
| 37 | Phthaloyl dichloride | 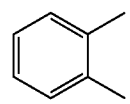 |
| 38 | Isophthaloyl dichloride | 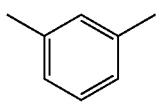 |
| 39 | Terephthaloyl dichloride | 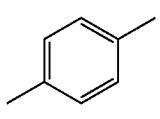 |
| 40 | Fumaryl chloride | —C=C— |
| 41 | Succinyl chloride | —(CH$_2$)$_2$— |
| 42 | Glutaryl chloride | —(CH$_2$)$_3$— |
| 43 | Adipoyl chloride | —(CH$_2$)$_4$— |
| 44 | Pimeloyl chloride | —(CH$_2$)$_5$— |

-continued

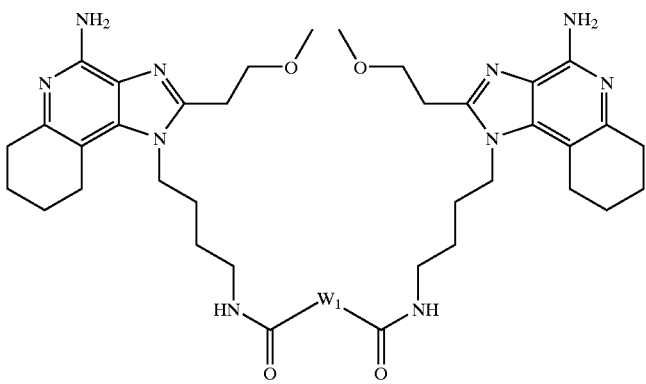

| Example | Diacid Dichloride | $W_1$ |
|---|---|---|
| 45 | Suberoyl chloride | —$(CH_2)_6$— |
| 46 | Azelaoyl chloride | —$(CH_2)_7$— |
| 47 | Sebacoyl chloride | —$(CH_2)_8$— |
| 48 | 2,6-Pyridinedicarbonyl dichloride | 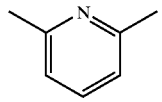 |
| 49 | Dodecanedioyl dichloride | —$(CH_2)_{10}$— |
| 50 | Tetrafluorosuccinyl chloride | —$(CF_2)_2$— |
| 51 | Tetrachloroterephthaloyl chloride | 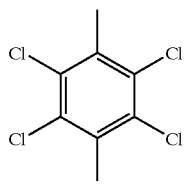 |
| 52 | Hexafluoroglutaryl chloride | —$(CF_2)_3$— |
| 53 | Octafluoroadipoyl chloride | —$(CF_2)_4$— |
| 54 | 4,4'-Benzoyl chloride | 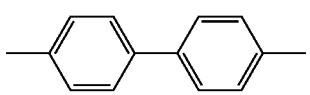 |
| 55 | 2,2'-Oxydiacetyl chloride | —$CH_2$—$O$—$CH_2$— |
| 56 | Trans-5-norbornene-2,3-dicarbonyl chloride | 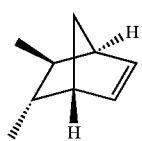 |

EXAMPLES 57–64

Using the general method of Example 5, 4-(4-amino-2-butyl-1H-imidazo[4,5-c][1,5]naphthyridin-1-yl)butaneamine (Example 46 in U.S. Pat. No. 6,194,425) can be reacted with a disulfonyl chloride from the table below to provide a dimer of the invention. All of the disulfonyl chlorides in the table are commercially available.

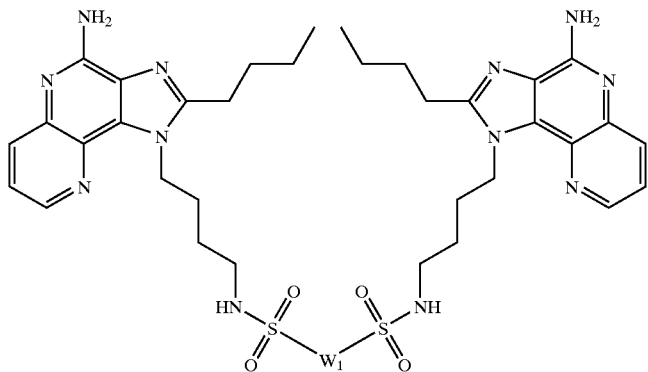

| Example | Disulfonyl Chloride | $W_1$ |
|---|---|---|
| 57 | 4,4'-Biphenyldisulfonyl chloride | 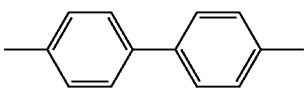 |
| 58 | 2,4-Mesitylenedisulfonyl dichloride | 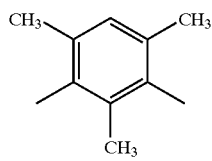 |
| 59 | 4,4'-Methylene-bis(benzenesulfonylchloride) | 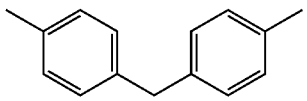 |
| 60 | 4,4'-Bis(chlorosulfonyl)diphenylether | 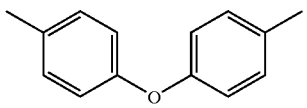 |
| 61 | 1,4-Butanedisulfonylchloride | —(CH$_2$)$_4$— |
| 62 | 1,3-Benzenedisulfonyl chloride | 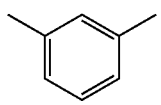 |
| 63 | 1,2-Benzenedisulfonyl chloride | 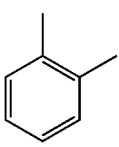 |
| 64 | 1,4-Bis(chlorosulfonyl)octafluorobutane | —(CF$_2$)$_4$— |

EXAMPLES 65–86

Using the general method of Example 2, 2-(4-amino-2-butyl-1H-imidazo[4,5-c][1,5]naphthyridin-1-yl)ethaneamine (Example 91 in U.S. Pat. No. 6,194,425) can be reacted with a diisocyanate from the table below to provide a dimer of the invention. All of the diisocyanates in the table are commercially available.

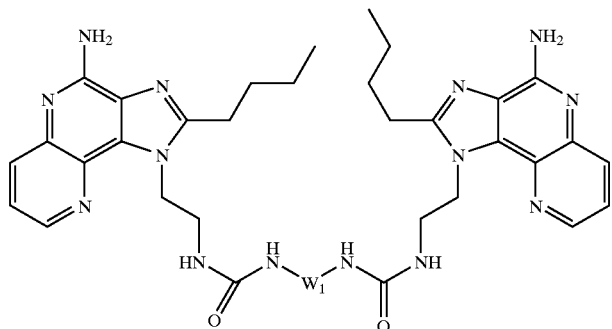
| Example | Diisocyanate | $W_1$ |
|---|---|---|
| 65 | Tolylene 2,6-diisocyanate | 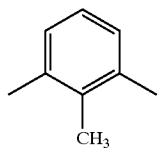 |
| 66 | 1,3-Phenylene diisocyanate | 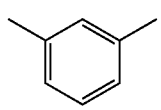 |
| 67 | 1,4-Phenylene diisocyanate | 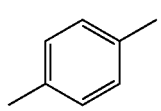 |
| 68 | Hexamethylene diisocyanate | —$(CH_2)_6$— |
| 69 | 3,3'-Bianisole-4,4'-isocyanic acid ester | 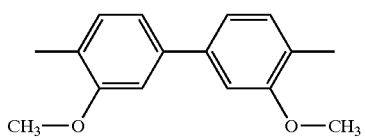 |
| 70 | Dicyclohexylmethane-4,4'-diisocyanate | 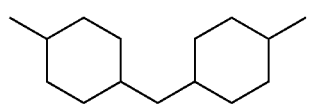 |
| 71 | 3,3'-Bitolyene-4,4'-diisocyanate | 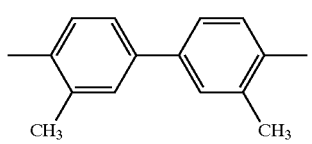 |
| 72 | 4,4'-Diisocyanato-3,3'-dimethyldiphenylmethane | 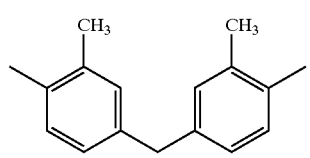 |
| 73 | m-Xylene diisocyanate | 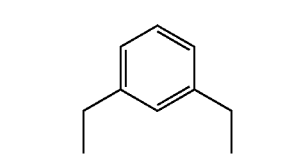 |
| 74 | 4,4'-Diphenylmethane diisocyanate | 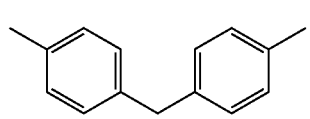 |

-continued

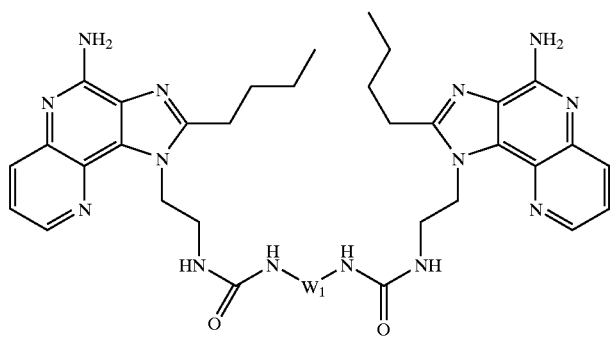

| Example | Diisocyanate | $W_1$ |
|---|---|---|
| 75 | 1,2-Diisocyanatododecane | —(CH$_2$)$_{12}$— |
| 76 | 4,4'-Methylenebis(2-chlorophenyl isocyanate) | 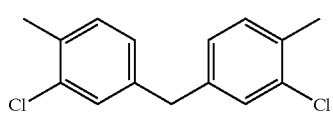 |
| 77 | 1,5-Naphthalenediisocyanate | 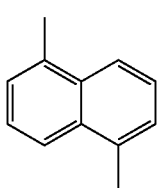 |
| 78 | 3,3'-Dichlorodiphenyl 4,4'-diisocyanate | 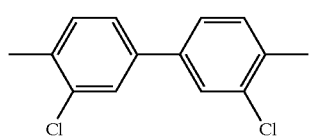 |
| 79 | Trans-1,4-cyclohexane diisocyanate | 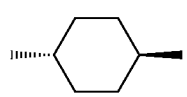 |
| 80 | 1,4-Diisocyanatobutane | —(CH$_2$)$_4$— |
| 81 | 1,3-Bis(isocyanatomethyl)cyclohexane | 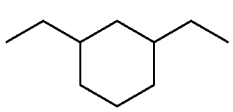 |
| 82 | 3,3',5,5'-Tetraethyldiphenylmethane-4,4'-diisocyanate | 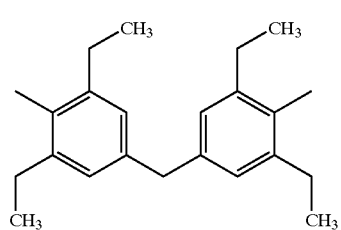 |
| 83 | 1,8-Diisocyanatooctane | —(CH$_2$)$_8$— |
| 84 | Oxybis(4-phenylisocyanate) | 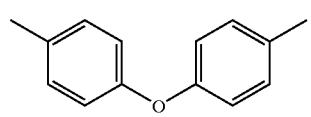 |

-continued

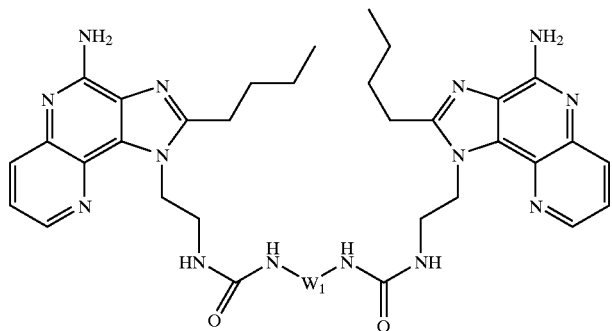

| Example | Diisocyanate | $W_1$ |
|---|---|---|
| 85 | 2,4,6-Trimethyl-1,3-phenylene diisocyanate | 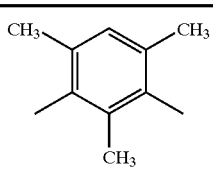 |
| 86 | 2,4'-Methylenebis(phenyl isocyanate) | 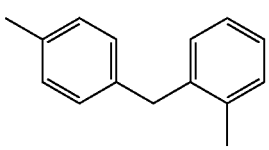 |

EXAMPLES 87–106

Using the general method of Example 6, 4-(4-amino-1H-imidazo[4,5-c][1,5]naphthyridin-1-yl)butaneamine (Example 111 in U.S. Pat. No. 6,194,425) can be reacted with a diacid dichloride from the table below to provide a dimer of the invention. All of the diacid dichlorides in the table are commercially available.

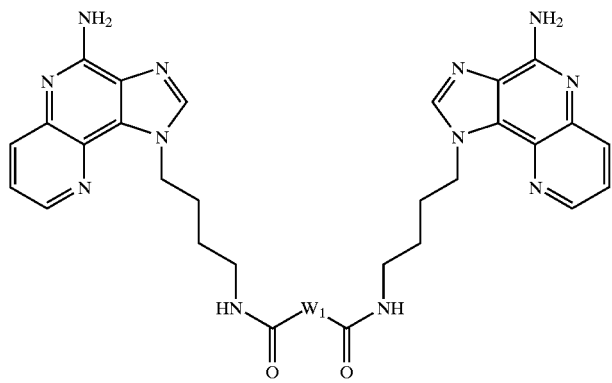

| Example | Diacid Dichloride | $W_1$ |
|---|---|---|
| 87 | Phthaloyl dichloride | 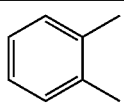 |
| 88 | Isophthaloyl dichloride | 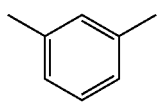 |

-continued

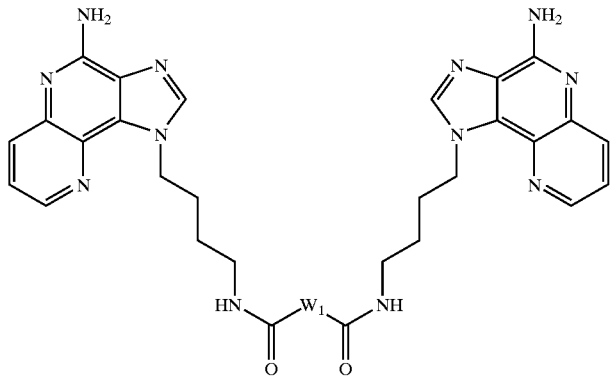

| Example | Diacid Dichloride | W₁ |
|---|---|---|
| 89 | Terephthaloyl dichloride | 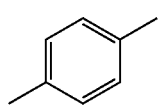 |
| 90 | Fumaryl chloride | —C=C— |
| 91 | Succinyl chloride | —(CH$_2$)$_2$— |
| 92 | Glutaryl chloride | —(CH$_2$)$_3$— |
| 93 | Adipoyl chloride | —(CH$_2$)$_4$— |
| 94 | Pimeloyl chloride | —(CH$_2$)$_5$— |
| 95 | Suberoyl chloride | —(CH$_2$)$_6$— |
| 96 | Azelaoyl chloride | —(CH$_2$)$_7$— |
| 97 | Sebacoyl chloride | —(CH$_2$)$_8$— |
| 98 | 2,6-Pyridinedicarbonyl dichloride | 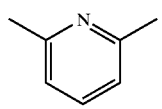 |
| 99 | Dodecanedioyl dichloride | —(CH$_2$)$_{10}$— |
| 100 | Tetrafluorosuccinyl chloride | —(CF$_2$)$_2$— |
| 101 | Tetrachloroterephthaloyl chloride | 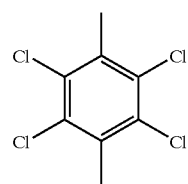 |
| 102 | Hexafluoroglutaryl chloride | —(CF$_2$)$_3$— |
| 103 | Octafluoroadipoyl chloride | —(CF$_2$)$_4$— |
| 104 | 4,4'-Benzoyl chloride | 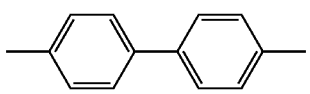 |
| 105 | 2,2'-Oxydiacetyl chloride | —CH$_2$—O—CH$_2$— |
| 106 | Trans-5-norbornene-2,3-dicarbonyl chloride | 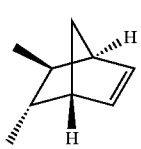 |

EXAMPLES 107–114

Using the general method of Example 5, 1-(4-aminobutyl)-2-(ethoxymethyl)-6-methyl-1H-imidazo[4,5-c]pyridin-4-amine (Example 10 in U.S. Pat. No. 6,545,016) can be reacted with a disulfonyl chloride from the table below to provide a dimer of the invention. All of the disulfonyl chlorides in the table are commercially available.

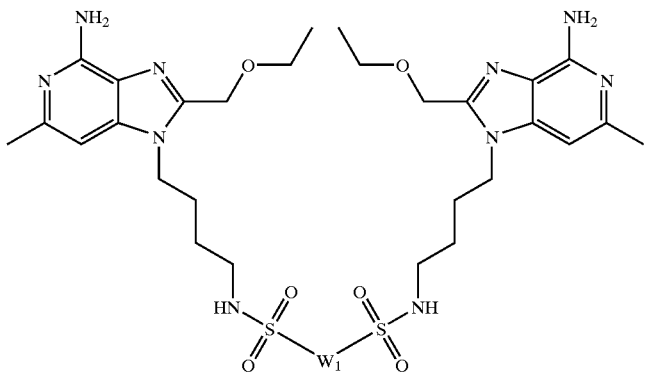

| Example | Disulfonyl Chloride | $W_1$ |
|---|---|---|
| 107 | 4,4'-Biphenyldisulfonyl chloride | |
| 108 | 2,4-Mesitylenedisulfonyl dichloride | |
| 109 | 4,4'-Methylene-bis(benzenesulfonylchloride) | |
| 110 | 4,4'-Bis(chlorosulfonyl)diphenylether | |
| 111 | 1,4-Butanedisulfonylchloride | —(CH$_2$)$_4$— |
| 112 | 1,3-Benzenedisulfonyl chloride | |
| 113 | 1,2-Benzenedisulfonyl chloride | |
| 114 | 1,4-Bis(chlorosulfonyl)octafluorobutane | —(CF$_2$)$_4$— |

EXAMPLES 115–136

Using the general method of Example 2, 1-(3-aminopropyl)-2,6,7-trimethyl-1H-imidazo[4,5-c]pyridin-4-amine (Example 18 in U.S. Pat. No. 6,545,016) can be reacted with a diisocyanate from the table below to provide a dimer of the invention. All of the diisocyanates in the table are commercially available.

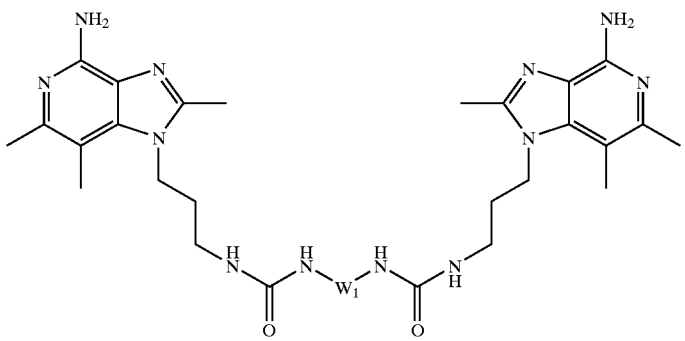

| Example | Diisocyanate | $W_1$ |
|---|---|---|
| 115 | Tolylene 2,6-diisocyanate | |
| 116 | 1,3-Phenylene diisocyanate | |
| 117 | 1,4-Phenylene diisocyanate | |
| 118 | Hexamethylene diisocyanate | $-(CH_2)_6-$ |
| 119 | 3,3'-Bianisole-4,4'-isocyanic acid ester | |
| 120 | Dicyclohexylmethane-4,4'-diisocyanate | |
| 121 | 3,3'-Bitolyene-4,4'-diisocyanate | |
| 122 | 4,4'-Diisocyanato-3,3'-dimethyldiphenylmethane | |

-continued

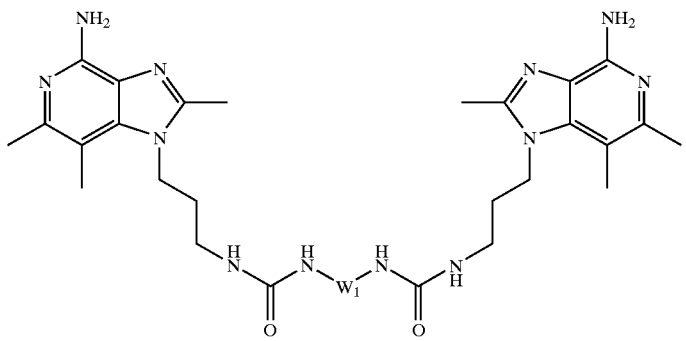

| Example | Diisocyanate | W₁ |
|---|---|---|
| 123 | m-Xylene diisocyanate | 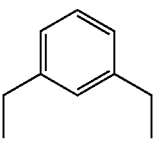 |
| 124 | 4,4'-Diphenylmethane diisocyanate | 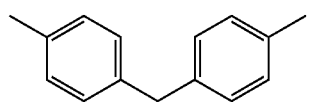 |
| 125 | 1,2-Diisocyanatododecane | —(CH$_2$)$_{12}$— |
| 126 | 4,4'-Methylenebis(2-chlorophenyl isocyanate) | 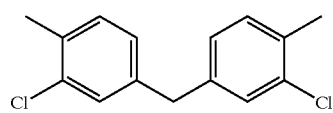 |
| 127 | 1,5-Naphthalenediisocyanate | 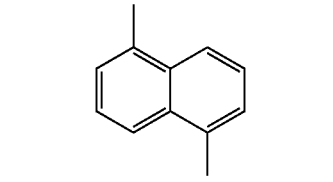 |
| 128 | 3,3'-Dichlorodiphenyl 4,4'-diisocyanate | 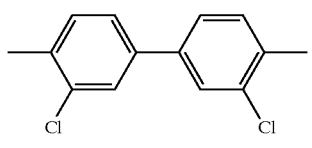 |
| 129 | Trans-1,4-cyclohexane diisocyanate |  |
| 130 | 1,4-Diisocyanatobutane | —(CH$_2$)$_4$— |
| 131 | 1,3-Bis(isocyanatomethyl)cyclohexane | 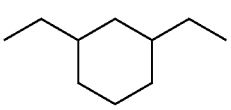 |
| 132 | 3,3',5,5'-Tetraethyldiphenylmethane-4,4'-diisocyanate | 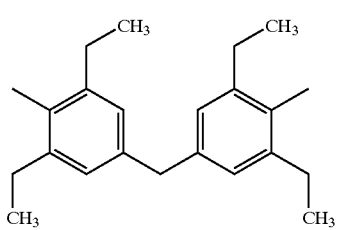 |

-continued

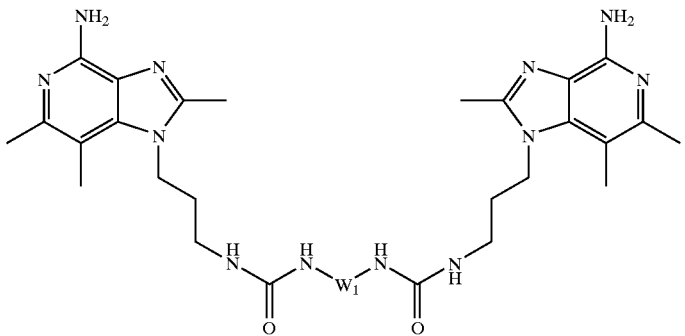

| Example | Diisocyanate | $W_1$ |
|---|---|---|
| 133 | 1,8-Diisocyanatooctane |  —(CH$_2$)$_8$— |
| 134 | Oxybis(4-phenylisocyanate) | 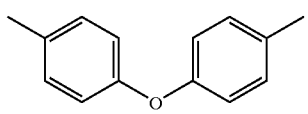 |
| 135 | 2,4,6-Trimethyl-1,3-phenylene diisocyanate | 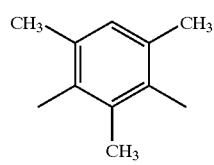 |
| 136 | 2,4'-Methylenebis(phenyl isocyanate) | 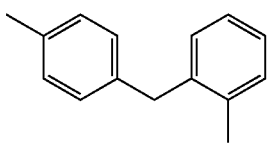 |

EXAMPLES 137–156

Using the general method of Example 6, 1-(4-aminobutyl)-2-(ethoxymethyl)-7-methyl-1H-imidazo[4,5-c]pyridin-4-amine (Example 26 in U.S. Pat. No. 6,545,016) can be reacted with a diacid dichloride from the table below to provide a dimer of the invention. All of the diacid dichlorides in the table are commercially available.

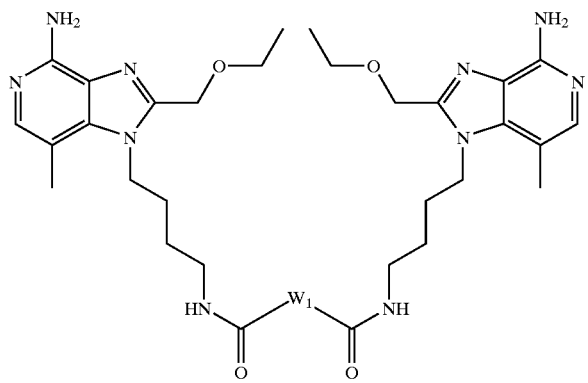

| Example | Diacid Dichloride | W₁ |
|---|---|---|
| 137 | Phthaloyl dichloride | 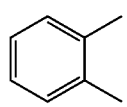 |
| 138 | Isophthaloyl dichloride | 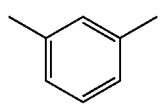 |
| 139 | Terephthaloyl dichloride | 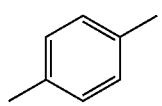 |
| 140 | Fumaryl chloride | —C=C— |
| 141 | Succinyl chloride | —(CH$_2$)$_2$— |
| 142 | Glutaryl chloride | —(CH$_2$)$_3$— |
| 143 | Adipoyl chloride | —(CH$_2$)$_4$— |
| 144 | Pimeloyl chloride | —(CH$_2$)$_5$— |
| 145 | Suberoyl chloride | —(CH$_2$)$_6$— |
| 146 | Azelaoyl chloride | —(CH$_2$)$_7$— |
| 147 | Sebacoyl chloride | —(CH$_2$)$_8$— |
| 148 | 2,6-Pyridinedicarbonyl dichloride | 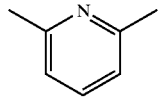 |
| 149 | Dodecanedioyl dichloride | —(CH$_2$)$_{10}$— |
| 150 | Tetrafluorosuccinyl chloride | —(CF$_2$)$_2$— |
| 151 | Tetrachloroterephthaloyl chloride | 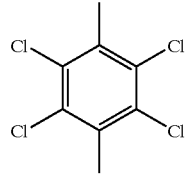 |
| 152 | Hexafluoroglutaryl chloride | —(CF$_2$)$_3$— |
| 153 | Octafluoroadipoyl chloride | —(CF$_2$)$_4$— |
| 154 | 4,4'-Benzoyl chloride | 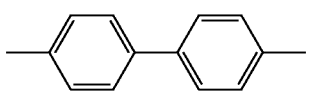 |
| 155 | 2,2'-Oxydiacetyl chloride | —CH$_2$—O—CH$_2$— |

-continued

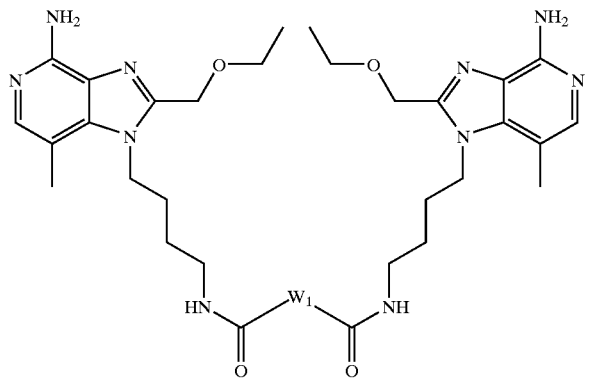

| Example | Diacid Dichloride | $W_1$ |
|---|---|---|
| 156 | Trans-5-norbornene-2,3-dicarbonyl chloride | 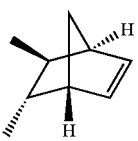 |

Cytokine Induction In Human Cells

An in vitro human blood cell system is used to assess cytokine induction. Activity is based on the measurement of interferon and tumor necrosis factor (α) (IFN and TNF, respectively) secreted into culture media as described by Testerman et. al. In "Cytokine Induction by the Immunomodulators Imiquimod and S-27609", Journal of Leukocyte Biology, 58, 365–372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using Histopaque® 1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at $4 \times 10^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30–0.014 μM.

Incubation

The solution of test compound is added at 60 μM to the first well containing RPMI complete and serial 3 fold dilutions are made in the wells. The PBMC suspension is then added to the wells in an equal volume; bringing the test compound concentrations to the desired range (30–0.014 μM). The final concentration of PBMC suspension is $2 \times 10^6$ cells/mL. The plates are covered with, sterile plastic lids, mixed gently and then incubated for 18 to 24 hours at 37° C. in a 5% carbon dioxide atmosphere.

Separation

Following incubation the plates are centrifuged for 10 minutes at 1000 rpm (~200×g) at 4° C. The cell-free culture supernatant is removed with a sterile polypropylene pipet and transferred to sterile polypropylene tubes. Samples are maintained at −30 to −70° C. until analysis. The samples are analyzed,for interferon (α) by ELISA and for tumor necrosis factor (α) by ELISA or IGEN Assay.

Interferon (α) and Tumor Necrosis Factor (α) Analysis by ELISA

Interferon (α) concentration is determined by ELISA using a Human Multi-Species kit from PBL Biomedical Laboratories, New Brunswick, N.J. Results are expressed in pg/mL.

Tumor necrosis factor (α) (TNF-α) concentration is determined using ELISA kits available from Biosource International, Camarillo, Calif. Alternately, the TNF-α concentration can be determined by Origen® M-Series Immunoassay and read on an IGEN M-8 analyzer from IGEN International, Gaithersburg, Md. The immunoassay uses a human TNF-α capture and detection antibody pair from Biosource International, Camarillo, Calif. Results are expressed in pg/mL.

Compounds of the invention were tested for their ability to induce cytokine biosynthesis using the method described above. The results are summarized in the table below where a "+" indicates that at concentrations of ≦10 μM the compound induced the indicated cytokine, a "−" indicates that at concentrations of ≦10 μM the compound did not induce the indicated cytokine, and a "*" indicates that the compound was not adequately soluble in DMSO to permit testing.

| Cytokine Induction in Human Cells | | |
|---|---|---|
| Compound of Example | Interferon (α) | Tumor Necrosis Factor (α) |
| 1 | + | + |
| 2 | + | + |
| 3 | + | + |
| 4 | + | + |
| 5 | + | + |

-continued

| Cytokine Induction in Human Cells | | |
|---|---|---|
| Compound of Example | Interferon (α) | Tumor Necrosis Factor (α) |
| 6 | + | + |
| 7 | + | + |
| 8 | * | * |

The complete disclosures of the patents, patent documents, and publications cited herein are incorporated by reference in their entirety as if each were individually incorporated. The present invention has been described with reference to several embodiments thereof. The foregoing illustrative embodiments and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention is intended to be limited only by the claims that follow.

What is claimed is:

1. A compound of the formula (I):

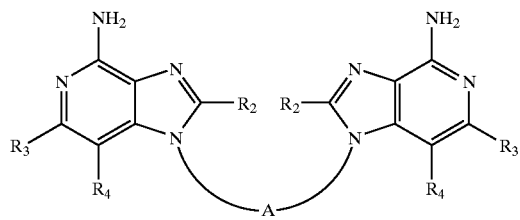

(I)

wherein:
A is a divalent linking group selected from the group consisting of:
straight or branched chain $C_{4-20}$ alkylene;
straight or branched chain $C_{4-20}$ alkenylene;
straight or branched chain $C_{4-20}$ alkynylene; and
—Z—Y—W—Y—Z—;
each Z is independently selected from the group consisting of:
straight or branched chain $C_{2-20}$ alkylene;
straight or branched chain $C_{4-20}$ alkenylene; and
straight or branched chain $C_{4-20}$ alkynylene;
any of which may be optionally interrupted by —O—, —N($R_5$)—, or —S(O)$_2$—;
each Y is independently selected from the group consisting of:
a bond;
—N($R_5$)C(O)—;
—C(O)N($R_5$)—;
—N($R_5$)C(O)N($R_5$)—;
—N($R_5$)S(O)$_2$—;
—S(O)$_2$N($R_5$)—;
—OC(O)O—;
—OC(O)—;
—C(O)O—;
—N($R_5$)C(O)O—; and
—OC(O)N($R_5$)—;
W is selected from the group consisting of:
straight or branched chain $C_{2-20}$ alkylene;
straight or branched chain $C_{2-20}$ alkenylene;
straight or branched chain $C_{4-20}$ alkynylene;
straight or branched chain perfluoro $C_{2-20}$ alkylene;
$C_{1-4}$ alkylene-O—$C_{1-4}$ alkylene;
—C(O)—;
—S(O)$_2$—;
—OC(O)O—;
—N($R_5$)C(O)N($R_5$)—;

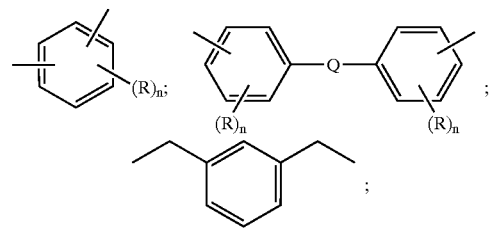

1,5-naphthylene;
2,6-pyridinylene;
1,2-cyclohexylene;
1,3-cyclohexylene;
1,4-cyclohexylene;
trans-1,4-cyclohexylene;

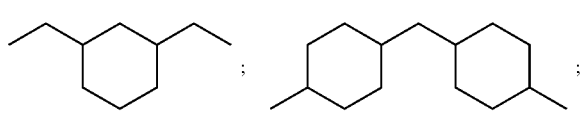

and
trans-5-norbornen-2,3-diyl;
wherein n is 0–4; each R is independently selected from the group consisting of $C_{1-4}$ alkyl, $C_{1-4}$ alkoxy, and halogen; and Q is selected from the group consisting of a bond, —CH$_2$—, and —O—;
$R_2$ is selected from the group consisting of:
-hydrogen;
-alkyl;
-alkenyl;
-aryl;
-substituted aryl;
-heteroaryl;
-substituted heteroaryl;
-alkyl-X-alkyl;
-alkyl-X-aryl;
-alkyl-X-alkenyl; and
-alkyl or alkenyl substituted by one or more substituents selected from the group consisting of:
—OH;
-halogen;
—N($R_6$)$_2$;
—C(O)—N($R_6$)$_2$;
—C(S)—N($R_6$)$_2$;
—S(O)$_2$—N($R_6$)$_2$;
—N($R_6$)—C(O)—$C_{1-10}$ alkyl;
—N($R_6$)—C(S)—$C_{1-10}$ alkyl;
—N($R_6$)—S(O)$_2$—$C_{1-10}$ alkyl;
—C(O)—$C_{1-10}$ alkyl;
—C(O)—O—$C_{1-10}$ alkyl;
—N$_3$;
-aryl;
-substituted aryl;
-heteroaryl;
-substituted heteroaryl;
-heterocyclyl;

-substituted heterocyclyl;
—C(O)-aryl;
—C(O)-(substituted aryl);
—C(O)-heteroaryl; and
—C(O)-(substituted heteroaryl);

$R_3$ and $R_4$ are each independently selected from the group consisting of:
-hydrogen;
-halogen;
-alkyl;
-alkenyl;
-X-alkyl; and
—$N(R_6)_2$;
or when taken together, $R_3$ and $R_4$ form a fused aryl or heteroaryl ring that is unsubstituted or substituted by one or more substituents selected from the group consisting of:
-halogen;
-alkyl;
-alkenyl;
-X-alkyl; and
—$N(R_6)_2$;
or when taken together, $R_3$ and $R_4$ form a fused 5 to 7 membered saturated ring, containing 0 to 2 heteroatoms and unsubstituted or substituted by one or more substituents selected from the group consisting of:
-halogen;
-alkyl;
-alkenyl;
-X-alkyl; and
—$N(R_6)_2$;

each $R_5$ is independently selected from the group consisting of:
hydrogen;
$C_{1-6}$ alkyl;
$C_{3-7}$ cycloalkyl; and
benzyl; or when Y is —$N(R_5)C(O)$—, —$C(O)N(R_5)$—, —$N(R_5)C(O)N(R_5)$—, —$N(R_5)S(O)_2$—, —$S(O_2)N(R_5)$—, —$N(R_5)C(O)O$—, or —$OC(O)N(R_5)$— and the nitrogen of the $N(R_5)$ group is bonded to Z, then $R_5$ can join with Z to form a ring having the structure

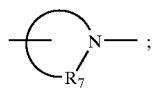

each $R_6$ is independently hydrogen or $C_{1-10}$ alkyl;
$R_7$ is $C_{3-8}$ alkylene; and
X is —O— or —S—;
with the proviso that if W is —C(O)—, —S(O)$_2$—, —OC(O)O—, or —$N(R_5)C(O)N(R_5)$— then each Y is a bond;
or a pharmaceutically acceptable salt thereof.

2. A compound or salt of claim 1 wherein A is straight or branched chain $C_{4-20}$ alkylene.

3. A compound or salt of claim 1 wherein A is —Z—Y—W—Y—Z—.

4. A compound or salt of claim 3 wherein Z is straight or branched chain $C_{2-20}$ alkylene optionally interrupted by —O—.

5. A compound or salt of claim 4 wherein Z is selected from the group consisting of straight or branched chain $C_{2-4}$ alkylene and $C_{1-4}$ alkylene-O—$C_{1-4}$ alkylene.

6. A compound or salt of claim 3 wherein $R_5$ is joined with Z to form a ring having the structure

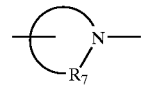

wherein $R_7$ is $C_{4-6}$ alkylene.

7. A compound or salt of claim 3 wherein each Y is independently selected from the group consisting of:
a bond;
—$N(R_5)C(O)$—;
—$C(O)N(R_5)$—;
—$N(R_5)C(O)N(R_5)$—;
—$S(O)_2N(R_5)$; and
—$N(R_5)S(O)_2$—.

8. A compound or salt of claim 7 wherein $R_5$ is hydrogen.

9. A compound or salt of claim 3 wherein W is selected from the group consisting of
straight or branched chain $C_{2-20}$ alkylene;
—$N(R_5)C(O)N(R_5)$—;

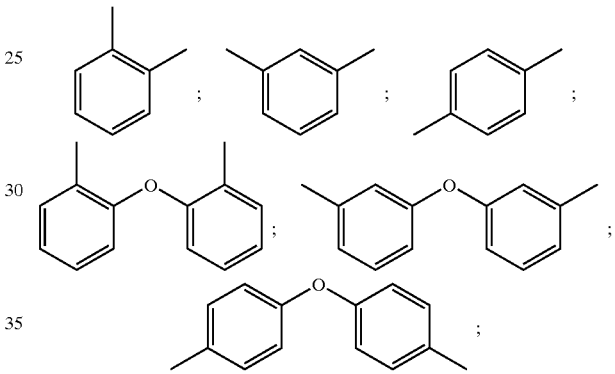

1,2-cyclohexylene;
1,3-cyclohexylene;
1,4-cyclohexylene; and
trans-1,4-cyclohexylene.

10. A compound or salt of claim 1 wherein $R_2$ is selected from the group consisting of hydrogen, alkyl, and alkyl-O-alkyl.

11. A compound or salt of claim 10 wherein $R_2$ is selected from the group consisting of hydrogen, methyl, ethyl, propyl, butyl, cyclopropylmethyl, ethoxymethyl and methoxyethyl.

12. A compound or salt of claim 1 wherein $R_3$ and $R_4$ taken together form a fused benzene ring.

13. A compound or salt of claim 1 wherein $R_3$ and $R_4$ taken together form a fused pyridine ring.

14. A compound or salt of claim 1 wherein $R_3$ and $R_4$ taken together form a six membered saturated ring.

15. A compound or salt of claim 1 wherein $R_3$ and $R_4$ taken together form a six membered saturated ring containing a nitrogen atom.

16. A compound or salt of claim 1 wherein $R_3$ and $R_4$ are independently selected from the group consisting of hydrogen and alkyl.

17. A compound selected from the group consisting of
N,N'-bis[4-(4-amino-2-butyl-1H-imidazo[4,5-c]quinolin-1-yl)butyl]urea;
N,N''-1,3-phenylenebis{N'-[4-(4-amino-2-butyl-1H-imidazo[4,5-c]-quinolin-1-yl)butyl]urea};

N-[4-(4-(amino-2-butyl-1H-imidazo[4,5-c]quinolin-1-yl)butyl]-N'-(4-{4-[({[4-(4-amino-2-butyl-1H-imidazo[4,5-c]quinolin-1-yl)butyl]amino}carbonyl)amino]phenoxy}phenyl)urea;

N,N"-trans-1,4-cyclohexylenebis{N'-[4-(4-amino-2-butyl-1H-imidazo[4,5-c]quinolin-1-yl)butyl]urea};

N,N'-bis(2-{2-[4-amino-2-(2-methoxyethyl)-1H-imidazo[4,5-c]quinolin-1-yl]ethoxy}ethyl)benzene-1,3-disulfonamide;

N,N'-bis(2-{2-[4-amino-2-(2-methoxyethyl)-1H-imidazo[4,5-c]quinolin-1-yl]ethoxy}ethyl)terephthalamide;

N,N"-1,8-octanediylbis[N'-(2-{2-[4-amino-2-(methoxyethyl)-1H-imidazo[4,5-c]quinolin-1-yl]ethoxy}ethyl)urea]; and 1-[10-(4-amino-2-ethoxymethyl-1H-imidazo[4,5-c]quinolin-1-yl)decyl]-2-ethoxymethyl-1H-imidazo[4,5-c]quinoline-4-amine;

or a pharmaceutically acceptable salt thereof.

18. A pharmaceutical composition comprising a therapeutically effective amount of a compound or salt of claim 1 and a pharmaceutically acceptable carrier.

19. A pharmaceutical composition comprising a therapeutically effective amount of a compound or salt of claim 17 and a pharmaceutically acceptable carrier.

20. A method of inducing biosynthesis of interferon or tumor necrosis factor in an animal comprising administering an effective amount of a compound or salt of claim 1 to the animal.

21. The method of claim 20 wherein the compound or salt is administered topically.

22. A method of inducing biosynthesis of interferon or tumor necrosis factor in an animal comprising administering an effective amount of a compound or salt of claim 17 to the animal.

23. The method of claim 22 wherein the compound or salt is administered topically.

* * * * *

UNITED STATES PATENT AND TRADEMARK OFFICE
CERTIFICATE OF CORRECTION

PATENT NO. : 6,818,650 B2
DATED : November 16, 2004
INVENTOR(S) : Griesgraber, George W.

It is certified that error appears in the above-identified patent and that said Letters Patent is hereby corrected as shown below:

Column 3,
Line 26, after "of" insert -- : --;

Column 5,
Lines 20-21, delete "N($R_5$)C(O)N($R_5$", insert in place thereof -- N($R_5$)C(O)N($R_5$) --;

Column 6,
Line 8, after "thereof", insert -- . --;

Column 7,
Line 20, delete "aryl,", insert in place thereof -- aryl; --;
Line 37, after "thereof", insert -- . --;

Formula (V), delete " 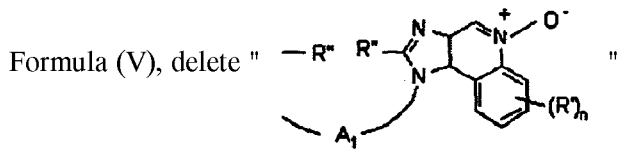 "

insert in place thereof -- 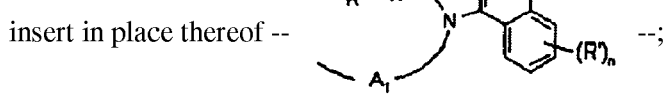 --;

Column 8,
Line 35, after "thereof", insert -- . --;

Column 9,
Line 13, insert -- 1, -- before "2-cyclohexylene";

Column 10,
Line 23, after "thereof", insert -- . --;
Line 51, delete "arylsulfonyl chorides", insert in place thereof -- arylsulfonyl chlorides --;
Line 52, delete "benzenesulfonyl choride", insert in place thereof -- benzenesulfonyl chloride --;
Line 52, delete "methanesulfonyl choride", insert in place thereof -- methanesulfonyl chloride --;
Line 55, delete "animating", insert in place thereof -- aminating --;
Line 64, delete "At", insert in place thereof -- $A_1$ --;

UNITED STATES PATENT AND TRADEMARK OFFICE
CERTIFICATE OF CORRECTION

PATENT NO. : 6,818,650 B2
DATED : November 16, 2004
INVENTOR(S) : Griesgraber, George W.

It is certified that error appears in the above-identified patent and that said Letters Patent is hereby corrected as shown below:

Column 12,
Formula III (Reaction Scheme I), delete " 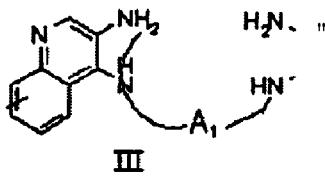 "

insert in place therefor -- 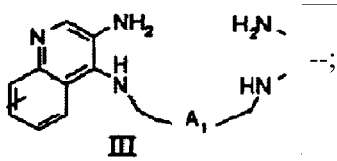 --;

Column 16,
Line 57, delete "dichioromethane", insert in place thereof -- dichloromethane --;

Column 18,
Formula XXIII (Reaction Scheme VIII) delete " 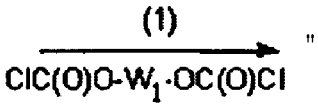 "

insert in place thereof --  --;

Line 57, delete "dichioromethane", insert in place thereof -- dichloromethane --;

Column 19,
Line 42, delete "tert-butyoxy", insert in place thereof -- tert-butyloxy --;
Line 61, delete "alkyl"."; insert in place thereof -- alkyl", --;

Column 20,
Line 18, delete "isotiazolidinyl", insert in place thereof -- isothiazolidinyl --;

Column 22,
Line 4, delete "initraepithelial", insert in place thereof -- intraepithelial --;

Column 23,
Line 67, after "(t, J=5.6 Hz, 2H)" insert -- , --;

UNITED STATES PATENT AND TRADEMARK OFFICE
CERTIFICATE OF CORRECTION

PATENT NO.  : 6,818,650 B2
DATED       : November 16, 2004
INVENTOR(S) : Griesgraber, George W.

It is certified that error appears in the above-identified patent and that said Letters Patent is hereby corrected as shown below:

Column 24,
Line 54, insert -- , -- before "4.53";
Line 63, after "Found" insert -- : --;

Column 25,
Line 27, delete "oxybisphenyl isocyanate)", insert in place thereof -- oxybis(phenyl isocyanate) --;
Line 62, delete "$^{13}$C N", insert in place thereof -- $^{13}$C NMR --;

Column 27,
Line 40, delete "quinotin", insert in place thereof -- quinolin --;
Line 50, delete "$NH_4H$", insert in place thereof -- $NH_4OH$ --;
Line 58, delete "4H,", insert in place thereof -- 4H), --;
Line 58, delete "4H),", insert in place thereof -- 4H); --;

Column 28,
Line 46, delete "$DMSO_6$", insert in place thereof -- $DMSO\text{-}d_6$ --;

Column 29,
Line 43, delete "a;", insert in place thereof -- a --;
Line 45, delete "C.", insert in place thereof -- C; --;
Line 51, delete "(t, J=5.0 Hz, 4H);", insert in place thereof -- (t, J=5.0 Hz, 4H), --;

Column 30,
Formula (Example 8), delete " 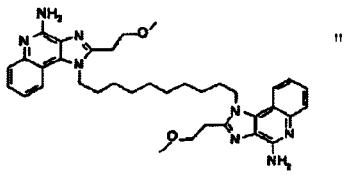 "

insert in place thereof -- 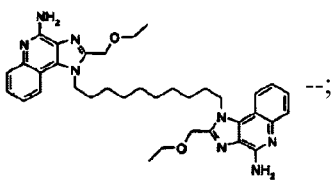 --;

UNITED STATES PATENT AND TRADEMARK OFFICE
CERTIFICATE OF CORRECTION

PATENT NO. : 6,818,650 B2
DATED : November 16, 2004
INVENTOR(S) : Griesgraber, George W.

It is certified that error appears in the above-identified patent and that said Letters Patent is hereby corrected as shown below:

Column 32,
Line 23, delete "15.1;", insert in place thereof -- 15.1. --;

Column 39,
Line 29, delete "2-methoxyethyl)", insert in place thereof -- 2-(methoxyethyl) --;

Column 63,
Line 39, delete "Histopaque® 1077", insert in place thereof -- Histopaque®- 1077 --;
Line 59, delete "volume;", insert in place thereof -- volume, --;
Line 62, after "with" delete ",";

Column 64,
Line 31, delete "analyzed,for", insert in place thereof -- analyzed for --;

Column 68,
Line 63, after "of" insert -- : --;
Line 67, delete "[4,5-c]-quinolin", insert in place thereof -- [4,5-c]quinolin --;

Column 69,
Line 1, delete "(4-(amino", insert in place thereof -- (4-amino --.

Signed and Sealed this

Thirtieth Day of August, 2005

JON W. DUDAS
*Director of the United States Patent and Trademark Office*